(12) United States Patent
Poulsen

(10) Patent No.: US 6,379,968 B1
(45) Date of Patent: Apr. 30, 2002

(54) TRANSGENIC PLANTS OR ALGAE EXPRESSING AN AGP ENZYME COUPLED TO A TRANSIT PEPTIDE

(75) Inventor: Peter Poulsen, Copenhagen (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/335,234

(22) Filed: Jun. 17, 1999

Related U.S. Application Data

(63) Continuation of application No. 08/535,276, filed as application No. PCT/EP94/01082 on Apr. 7, 1994, now Pat. No. 5,977,437.

(30) Foreign Application Priority Data

Apr. 8, 1993 (GB) .............................................. 9307408

(51) Int. Cl.[7] .......................... C12N 15/82; C12P 19/04; C12P 21/06; A01H 1/00
(52) U.S. Cl. ...................... 435/468; 435/101; 435/69.1; 435/69.8; 435/410; 435/419; 800/284; 800/287; 800/263
(58) Field of Search ................................ 435/468, 101, 435/69.1, 69.8, 410, 419; 800/278, 284, 263, 287, 295, 296, 298, 317; 536/23.6

(56) References Cited

FOREIGN PATENT DOCUMENTS

| EP | 0 368 5056 A2 | 5/1990 |
|---|---|---|
| EP | 0 455 316 A1 | 11/1991 |
| WO | WO 91/19806 | 12/1991 |
| WO | WO 92/11382 | 7/1992 |
| WO | WO 92/14827 | 9/1992 |

OTHER PUBLICATIONS

Ball et al., Planta, 185(1): 17–26 (1991).
Beck et al., Gene, 19: 327–336 (1982).
Brisson et al., The Plant Cell, 1: 559–566 (1989).
Caplan et al., Science 222: 815–821 (1983).
Fling et al., Nucleic Acids Res., 19: 7095–7106 (1985).
Gavel & Von Heine, FEBS Lett., 261: 455–458 (1990).
Hodal et al., Plant Science, 87: 115–122 (1992).
Itoh and Haas, Gene, 36: 27–36 (1985).
Itoh et al., Plasmid, 11: 206–220 (1984).
Jefferson et al., Proc. Natl. Acad. Sci. USA, 83: 8447–8451 (1986).
Kawasaki et al., Mol. Gen. Genet., 237: 10–16 (1993).
Kay et al., Science, 236: 1299–1302 (1987).
Kleczkowski et al., J. Biol. Chem., 268(9): 6228–6233 (1993).
Kleczkowski et al., Plant ADP–Gluc., Recent Adv. and Biotech Persp. (A Review), 46c: 605–613 (1991).
Kleczkowski, et al. Plant ADP–Gluc., Pyrophos.—Recent Adv. and Biotech. Perspect. (A Review). pp. 605–612. (1991).
Kleczkowski, et al. Plant Physiol.—Insensitivity of Barley Endosperm ADP–Glucose Pyrophosphorylase to 3–Phosphoglycerate and Orthophosphate Regulation. vol. 101, pp. 179–186. (1993).
Kleczkowski et al., Trends Plant Sci., 1(11): 363–364 (Nov. 1996).
Klosgen et al., Mol. Gen. Genet., 217: 155–161 (1989).
Linsmaier and Skoog, Physiol. Plant., 18 : 100–127 (1965).
Mignery et al., Gene, 62: 27–44 (1988).
Miles and Guest, Gene, 32: 41–48 (1984).
Odell et al., Nature, 313: 810–812 (1985).
Radke et al., Theor. Appl. Genet., 75: 685–694 (1988).
Stark et al., Science, 258: 287–292 (1992).
Van der Leij et al., Mol. Gen. Genet., 228: 240–248 (1991).
Villand et al., Plant Molecular Biology, 19: 381–389 (1992).
Villand et al., Plant Physiol., 100: 1617–1618 (1992).
Werneke et al., Proc. Natl. Acad. Sci., USA, 85: 787–791 (1988).
Yadav et al., Proc. Natl. Acad. Sci., USA, 79: 6322–6326 (1982).
Yamisch–Perron et al., Gene, 33: 103–117 (1985).

Primary Examiner—Andrew Wang
Assistant Examiner—Konstantina Katcheves
(74) Attorney, Agent, or Firm—Knobbe, Martens, Olson & Bear, LLP

(57) ABSTRACT

The present invention relates to transgenic plants or algae expressing an AGP enzyme coupled to a transit peptide. In particular, the present invention relates to transgenic plants or algae in which the activity of the AGP enzyme or subunit thereof is substantially independent of any level of in vivo 3-phospho-glycerate and any in vivo level of inorganic phosphate and wherein the activity of the AGP enzyme or subunit thereof is not stimulated by fructose-1,6-bisP and is not inhibited by AMP.

7 Claims, 13 Drawing Sheets

8.1 Amino terminal amino acid sequence of the rubisco activase - AGP small subunit fusion enzyme.

1    MATAVSTVGA ATRAPLNLNG SSAGASVPTS GFLGSSLKKH 40
41   TNVRFPSSSR TTSMTVKAAE NEEKNTDKWA HLAKDFSDDQ 80
81   LDIRRGKGMV DSLGSMDVPL ASKVPLPSPS KHEQCNVYSH 120

8.2 Amino terminal amino acid sequence of the rubisco activase - AGP large subunit fusion enzyme.

1    MATAVSTVGA ATRAPLNLNG SSAGASVPTS GFLGSSLKKH 40
41   TNVRFPSSSR TTSMTVKAAE NEEKNTDKWA HLAKDFSDDQ 80
81   LDIRRGKGMV DSLGIHMQFS SVLPLEGKAC VSPVRREGSA 120

8.3 Amino terminal amino acid sequence of the starch branching enzyme - AGP large subunit fusion enzyme.

1    MEINFKVLSK PIRGSFPSFS PKVSSGASRN KICFPSQHST 40
41   GLKFGSQERS WDISSTPKSR VRKDERMKHS SAISAVLTDD 80
81   NSTMAPLEED VKTENIGLLN LDPMQFSSVL PLEGKACVSP 120

FIG. 8

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 2037 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: Other
      (B) LOCATION: 1...2037
      (D) OTHER INFORMATION: cDNA encoding large subunit
          of ADP-glucose pyrophosphorylase (bep110)

(xi) SEQUENCE DESCRIPTION: SEQ ID NO:1:

```
ACGACCACCT CCGAACTCAA CGCCTCCACG GACCATCTCT CTCCTCTCCC CTCCCCTCAC      60

CACCACCACC ACCACCACCC CTTCTCCCTC CCTGCATTTG ATTCGTTCAT ATTCATCCGT     120

CGCTTGCCCG GTCGCCACCC CGTCGATCCC TCACCCCGCC GTCCCCGGCA GTTGCAGGTG     180
```

```
GACTGCTAAT GTCATCGATG CAGTTCAGCA GCGTGCTGCC CCTGGAGGGC AAGGCGTGCG    240

TTTCCCCAGT CAGGAGAGAG GGATCGGCCT GCGAGCGCCT CAAGATCGGG GACAGCAGCA    300

GCATCAGGCA CGAGAGAGCG TCCAGGAGGA TGTGCAACGG CGGCGCAGGG GCCCCGCCGC    360

CACCGGTGCG CAGTGCGTGC TCACCTCCGA CGCCAGCCCG GCCGACACCC TTGTTCTCCG    420

GACGTCCTTC CGGAGGAATT ACGCCGATCC GAACGAGGTC GCGGCCGTCG GTCGCGGCCG    480

TCATACTCGG CGGCGGCACC GGGACTCAGC TCTTCCCGCT CACAAGCACA AGGGCCACAC    540

CTGCTGTTCC TATTGGAGGA TGTTACAGGC TCATCGATAT TCCCATGAGC AACTGCTTCA    600

ACAGTGGCAT CAACAAGATA TTCGTCATGA CCCAGTTCAA CTCGGCATCT CTCAATCGCC    660

ACATTCACCG CACCTACCTC GGCGGGGGAA TCAATTTCAC TGATGGATCT GTTGAGGTAT    720

TGGCCGCGAC ACAAATGCCT GGGGAGGCTG CTGGATGGTT CCGCGGAACA GCGGATGCCG    780

TCAGAAAATT TATCTGGGTG CTTGAGGACT ACTATAAGCA TAAATCCATA GAGCACATTT    840

TGATCTTGTC GGGCGATCAG CTTTATCGCA TGGATTACAT GGAGCTTGTG CAGAAACATG    900

TGGATGACAA TGCTGACATT ACTTTATCAT GTGCCCCTGT GGAGAGAGC CGGGCATCTG    960

AGTACGGGCT AGTGAAGTTC GACAGTTCAG GCCGTGTGAT CCAGTTTTCT GAGAAGCCAA   1020

AGGGCGACGA TCTGGAAGCG ATGAAAGTGG ATACCAGTTT TCTCAATTTC GCCATAGACG   1080

ACCCTGCTAA ATATCCATAC ATTGCTTCGA TGGGAGTTTA TGTCTTCAAG AGAGATGTTC   1140

TGCTGAACCT TCTAAAGTCA AGATACGCAG AACTCATGA CTTTGGGTCT GAAATCCTCC   1200

CGAGAGCTCT GCATGATCAC AATGTACAGG CATATGTCTT CACTGACTAC TGGGAGGACA   1260

TTGGAACAAT CAGATCCTTC TTCGATGCGA ACATGGCCCT CTGCGAACAG CCTCCAAAGT   1320

TTGAATTTTA TGATCCAAAA ACCCCCTTCT TCACTTCGCC TCGGTACTTA CCGCCAACAA   1380

AGTCAGACAA GTGCAGGATC AAAGAAGCGA TCATTTCGCA CGGCTGCTTC TTGCGTGAAT   1440

GCAAAATCGA GCACTCCATC ATCGGCGTTC GTTCACGCCT AAACTCCGGA AGCGAGCTCA   1500

AGAACGCGAT GATGATGGGC GCGGACTCGT ACGAGACCGA GGACGAGATC TCGAGGCTGA   1560

TGTCTGAGGG CAAGGTTCCC ATCGGCGTCG GGGAGAACAC AAAGATCAGC AACTGCATCA   1620

TCGACATGAA CGCGAGGATA GGAAGGGACG TGGTCATCTC AAACAAGGAG GGGGTGCAAG   1680

AAGCCGACAG GCCGGAGGAA GGGTACTACA TCAGGTCCGG GATCGTGGTG ATCCAGAAGA   1740

ACGCGACCAT CAAGGACGGC ACCGTCGTGT AGGGCGTGCC GGGTCGGCGC GACGGGGTTC   1800

TGCGACAACC TGTGCGCTGC GTCGGTCGTC ATCATCTTCT CAAACTCCGG GACTGAAGAA   1860

GTGATCCGGG GACGGGAGAC GTTTGAAGCT TGAATGACTG AGACTGAAAG TGAAGGCGCA   1920

GCAGAGGCAG GCAGCATTAG TAGTAAGTAG TAAGTAAGTA GCAGTGGAAC AAAGTAATAG   1980

TCGTTCGTTT TTCCCCTGTA ATAAATAAGA GGCTGTGTGT TGAGGTAAAA AAAAAAA     2037
```

(2) INFORMATION FOR SEQ ID NO:2:

(i) SEQUENCE CHARACTERISTICS:
        (A) LENGTH: 1823 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Other
        (B) LOCATION: 1...1823
        (D) OTHER INFORMATION: cDNA encoding small subunit
            of ADP-glucose pyrophosphorylase of barley (xi) SEQUENCE DESCRIPTION: SEQ ID NO:2:

```
AAAAGTGAAC TCACACATCA CTCAATATCT ATATCCTTCC ATTTTATATC CCTCGGTGAT    60
GGATGTACCT TTGGCATCTA AAGTTCCCTT GCCCTCCCCT TCCAAGCATG AACAATGCAA   120
CGTTTATAGT CATAAGAGCT CATCGAAGCA TGCAGATCTC AATCCCCATG CTATTGATAG   180
TGTTCTCGGT ATCATTCTTG GAGGTGGTGC AGGGACTAGA TTGTATCCCC TGACGAAGAA   240
GCGTGCAAAG CCTGCAGTGC CATTGGGTGC CAACTACAGG CTTATTGATA TTCCTGTCAG   300
TAATTGTCTG AACAGCAACA TATCAAAGAT CTATGTGCTT ACACAGTTCA ACTCAGCTTC   360
TCTTAATCGT CATCTCTCAC GAGCCTATGG GAGCAACATT GGAGGTTACA AGAATGAAGG   420
ATTTGTTGAA GTCCTTGCTG CACAGCAGAG CCCAGATAAC CCTGACTGGT TCCAGGGTAC   480
TGCAGATGCT GTAAGGCAGT ACTTGTGGCT ATTCGAGGAG CATAATGTTA TGGAGTATCT   540
AATTCTTGCT GGAGATCACC TGTACCGAAT GGACTATGAA AAGTTTATTC AGGCACACAG   600
AGAAACGGAT GCTGATATTA CTGTTGCTGC CTTGCCCATG GATGAGGAAC GTGCAACTGC   660
ATTTGGCCTT ATGAAAATCG ATGAAGAAGG GAGGATAATT GAATTCGCAG AGAAACCAAA   720
AGGAGAACAG TTGAAAGCTA TGATGGTTGA TACGACCATA CTTGGCCTTG AAGATGCGAG   780
GGCAAAGGAA ATGCCTTATA TTGCTAGCAT GGGTATCTAT GTTATTAGCA ACATGTGAT   840
GCTTCAGCTT CTCCGTGAGC AATTTCCTGG AGCTAATGAC TTCGGAAGTG AAGTTATCCC   900
TGGTGCAACT AGCACTGGCA TGAGGGTACA AGCATACCTA TACGACGGTT ACTGGGAAGA   960
TATTGGTACA ATTGAGGCAT TCTATAATGC AAATTTGGGA ATTACCAAAA AACCAATACC  1020
TGATTTCAGT TTCTATGACC GTTCTGCTCC CATTTACACA CAACCTCGAC ACTTGCCTCC  1080
TTCAAAGGTT CTTGATGCTG ATGTGACAGA CAGTGTAATT GGTGAAGGAT GTGTTATTAA  1140
AAACTGCAAG ATACACCATT CAGTAGTTGG ACTCCGTTCC TGCATATCTG AAGGTGCAAT  1200
AATAGAGGAC ACGTTGCTAA TGGGTGCGGA CTACTATGAG ACTGAAGCTG ATAAGAAACT  1260
CCTTGCTGAA AAAGGTGGCA TTCCCATTGG TATTGGAAAG AATTCACACA TCAAAAGAGC  1320
AATCATTGAC AAGAATGCTC GTATTGGAGA TAACGTGATG ATAATCAATG TTGACAATGT  1380
TCAAGAAGCG GCGAGGGAGA CAGATGGATA CTTCATCAAA AGTGGCATCG TAACTGTGAT  1440
CAAGGATGCT TTACTCCCTA GTGGAACAGT CATATGAAGC AGATGTGAAA TGTATGCCAA  1500
AAGACAGGGC TACTTGCGTC AGTCTGGAAT CAACCAACAA GGCCGCGAAG GAGATCATAA  1560
AATAAAAARG GAGTGCCATG CGAGTCACTT CTACACCCTT TTCCCCCCTT GATGTATTAG  1620
GAACTGTGAT GTACAAGCAA CTGTGATGCA CTTACGCGAA GTGCCCCTGG ATTCAGCTTT  1680
CTCTTTGCTT GTAACTGGTT TCCAGCAGAC CATGCTATTT GTTGTATGGT TCGTGCAAAA  1740
CCTTGCGATG CTTTATATAT GCTTTATATA TAAACAAGAT GAATCCCCGC GCGTTGCTGC  1800
GGCACAAAAA AAAAAAAAAA AAA                                         1823
```

(2) INFORMATION FOR SEQ ID NO:3:

(i) SEQUENCE CHARACTERISTICS:
  (A) LENGTH: 527 amino acids
  (B) TYPE: amino acid
  (C) STRANDEDNESS: single
  (D) TOPOLOGY: linear (ii) MOLECULE TYPE: protein (ix) FEATURE:
  (A) NAME/KEY: Other
  (B) LOCATION: 1...528

(D) OTHER INFORMATION: Translation of cDNA encoding
       large subunit of ADP-glucose phosphorylse (xi) SEQUENCE DESCRIPTION: SEQ ID NO:3:

Met Ser Ser Met Gln Phe Ser Ser Val Leu Pro Leu Glu Gly Lys Ala
 1               5                  10                  15

Cys Val Ser Pro Val Arg Arg Glu Gly Ser Ala Cys Glu Arg Leu Lys
                20                  25                  30

Ile Gly Asp Ser Ser Ser Ile Arg His Glu Arg Ala Ser Arg Arg Met
            35                  40                  45

Cys Asn Gly Gly Ala Gly Ala Pro Pro Pro Val Arg Ser Ala Cys
 50                  55                  60

Ser Pro Pro Thr Pro Ala Arg Pro Thr Pro Leu Phe Ser Gly Arg Pro
 65                  70                  75                  80

Ser Gly Gly Ile Thr Pro Ile Arg Thr Arg Ser Arg Pro Ser Val Ala
                85                  90                  95

Ala Val Ile Leu Gly Gly Gly Thr Gly Thr Gln Leu Phe Pro Leu Thr
               100                 105                 110

Ser Thr Arg Ala Thr Pro Ala Val Pro Ile Gly Gly Cys Tyr Arg Leu
           115                 120                 125

Ile Asp Ile Pro Met Ser Asn Cys Phe Asn Ser Gly Ile Asn Lys Ile
       130                 135                 140

Phe Val Met Thr Gln Phe Asn Ser Ala Ser Leu Asn Arg His Ile His
145                 150                 155                 160

Arg Thr Tyr Leu Gly Gly Gly Ile Asn Phe Thr Asp Gly Ser Val Glu
                165                 170                 175

Val Leu Ala Ala Thr Gln Met Pro Gly Glu Ala Ala Gly Trp Phe Arg
            180                 185                 190

Gly Thr Ala Asp Ala Val Arg Lys Phe Ile Trp Val Leu Glu Asp Tyr
        195                 200                 205

Tyr Lys His Lys Ser Ile Glu His Ile Leu Ile Leu Ser Gly Asp Gln
        210                 215                 220

Leu Tyr Arg Met Asp Tyr Met Glu Leu Val Gln Lys His Val Asp Asp
225                 230                 235                 240

Asn Ala Asp Ile Thr Leu Ser Cys Ala Pro Val Gly Glu Ser Arg Ala
                245                 250                 255

Ser Glu Tyr Gly Leu Val Lys Phe Asp Ser Ser Gly Arg Val Ile Gln
            260                 265                 270

Phe Ser Glu Lys Pro Lys Gly Asp Asp Leu Glu Ala Met Lys Val Asp
        275                 280                 285

Thr Ser Phe Leu Asn Phe Ala Ile Asp Asp Pro Ala Lys Tyr Pro Tyr
    290                 295                 300

Ile Ala Ser Met Gly Val Tyr Val Phe Lys Arg Asp Val Leu Leu Asn
305                 310                 315                 320

Leu Leu Lys Ser Arg Tyr Ala Glu Leu His Asp Phe Gly Ser Glu Ile
                325                 330                 335

Leu Pro Arg Ala Leu His Asp His Asn Val Gln Ala Tyr Val Phe Thr
            340                 345                 350

Asp Tyr Trp Glu Asp Ile Gly Thr Ile Arg Ser Phe Asp Ala Asn
        355                 360                 365

Met Ala Leu Cys Glu Gln Pro Pro Lys Phe Glu Phe Tyr Asp Pro Lys
    370                 375                 380

Thr Pro Phe Phe Thr Ser Pro Arg Tyr Leu Pro Pro Thr Lys Ser Asp
385                 390                 395                 400

```
Lys Cys Arg Ile Lys Glu Ala Ile Ile Ser His Gly Cys Phe Leu Arg
                405                 410                 415

Glu Cys Lys Ile Glu His Ser Ile Ile Gly Val Arg Ser Arg Leu Asn
                420                 425                 430

Ser Gly Ser Glu Leu Lys Asn Ala Met Met Met Gly Ala Asp Ser Tyr
                435                 440                 445

Glu Thr Glu Asp Glu Ile Ser Arg Leu Met Ser Glu Gly Lys Val Pro
            450                 455                 460

Ile Gly Val Gly Glu Asn Thr Lys Ile Ser Asn Cys Ile Ile Asp Met
465                 470                 475                 480

Asn Ala Arg Ile Gly Arg Asp Val Val Ile Ser Asn Lys Glu Gly Val
                485                 490                 495

Gln Glu Ala Asp Arg Pro Glu Glu Gly Tyr Tyr Ile Arg Ser Gly Ile
                500                 505                 510

Val Val Ile Gln Lys Asn Ala Thr Ile Lys Asp Gly Thr Val Val
                515                 520                 525
```

(2) INFORMATION FOR SEQ ID NO:4:

(i) SEQUENCE CHARACTERISTICS:
        (A) LENGTH: 471 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...472
        (D) OTHER INFORMATION: translation of cDNA encoding
           small subunit of ADP-glucose phosphorylse (xi) SEQUENCE DESCRIPTION: SEQ ID NO:4:

```
Asp Val Pro Leu Ala Ser Lys Val Pro Leu Pro Ser Pro Ser Lys His
 1               5                  10                  15

Glu Gln Cys Asn Val Tyr Ser His Lys Ser Ser Ser Lys His Ala Asp
                20                  25                  30

Leu Asn Pro His Ala Ile Asp Ser Val Leu Gly Ile Ile Leu Gly Gly
                35                  40                  45

Gly Ala Gly Thr Arg Leu Tyr Pro Leu Thr Lys Lys Arg Ala Lys Pro
    50                  55                  60

Ala Val Pro Leu Gly Ala Asn Tyr Arg Leu Ile Asp Ile Pro Val Ser
65                  70                  75                  80

Asn Cys Leu Asn Ser Asn Ile Ser Lys Ile Tyr Val Leu Thr Gln Phe
                85                  90                  95

Asn Ser Ala Ser Leu Asn Arg His Leu Ser Arg Ala Tyr Gly Ser Asn
                100                 105                 110

Ile Gly Gly Tyr Lys Asn Glu Gly Phe Val Glu Val Leu Ala Ala Gln
            115                 120                 125

Gln Ser Pro Asp Asn Pro Asp Trp Phe Gln Gly Thr Ala Asp Ala Val
        130                 135                 140

Arg Gln Tyr Leu Trp Leu Phe Glu Glu His Asn Val Met Glu Tyr Leu
145                 150                 155                 160

Ile Leu Ala Gly Asp His Leu Tyr Arg Met Asp Tyr Glu Lys Phe Ile
                165                 170                 175

Gln Ala His Arg Glu Thr Asp Ala Asp Ile Thr Val Ala Ala Leu Pro
                180                 185                 190
```

```
Met Asp Glu Glu Arg Ala Thr Ala Phe Gly Leu Met Lys Ile Asp Glu
        195                 200                 205
Glu Gly Arg Ile Ile Glu Phe Ala Glu Lys Pro Lys Gly Glu Gln Leu
        210                 215                 220
Lys Ala Met Met Val Asp Thr Thr Ile Leu Gly Leu Glu Asp Ala Arg
225                 230                 235                 240
Ala Lys Glu Met Pro Tyr Ile Ala Ser Met Gly Ile Tyr Val Ile Ser
                245                 250                 255
Lys His Val Met Leu Gln Leu Leu Arg Glu Gln Phe Pro Gly Ala Asn
                260                 265                 270
Asp Phe Gly Ser Glu Val Ile Pro Gly Ala Thr Ser Thr Gly Met Arg
            275                 280                 285
Val Gln Ala Tyr Leu Tyr Asp Gly Tyr Trp Glu Asp Ile Gly Thr Ile
            290                 295                 300
Glu Ala Phe Tyr Asn Ala Asn Leu Gly Ile Thr Lys Lys Pro Ile Pro
305                 310                 315                 320
Asp Phe Ser Phe Tyr Asp Arg Ser Ala Pro Ile Tyr Thr Gln Pro Arg
                325                 330                 335
His Leu Pro Pro Ser Lys Val Leu Asp Ala Asp Val Thr Asp Ser Val
                340                 345                 350
Ile Gly Glu Gly Cys Val Ile Lys Asn Cys Lys Ile His His Ser Val
            355                 360                 365
Val Gly Leu Arg Ser Cys Ile Ser Glu Gly Ala Ile Ile Glu Asp Thr
        370                 375                 380
Leu Leu Met Gly Ala Asp Tyr Tyr Glu Thr Glu Ala Asp Lys Lys Leu
385                 390                 395                 400
Leu Ala Glu Lys Gly Gly Ile Pro Ile Gly Ile Gly Lys Asn Ser His
                405                 410                 415
Ile Lys Arg Ala Ile Ile Asp Lys Asn Ala Arg Ile Gly Asp Asn Val
            420                 425                 430
Met Ile Ile Asn Val Asp Asn Val Gln Glu Ala Ala Arg Glu Thr Asp
            435                 440                 445
Gly Tyr Phe Ile Lys Ser Gly Ile Val Thr Val Ile Lys Asp Ala Leu
        450                 455                 460
Leu Pro Ser Gly Thr Val Ile
465                 470

(2) INFORMATION FOR SEQ ID NO:5:

(i) SEQUENCE CHARACTERISTICS:
        (A) LENGTH: 480 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Other
        (B) LOCATION: 1...480
        (D) OTHER INFORMATION: Starch branching enzyme cDNA
            (First 480 nt from 5'end)

(xi) SEQUENCE DESCRIPTION: SEQ ID NO:5:

CCCGTCTGTA AGCATCATTA GTGATGTTGT TCCAGCTGAA TGGGATGATT CAGATGCAAA      60

CGTCTGGGGT GAGAACATAC AAGAAGGCAG CAGCTGAAGC AAAGTACCAT AATTTAATCA     120

ATGGAAATTA ATTTCAAAGT TTTATCAAAA CCCATTCGAG GATCTTTTCC ATCTTTCTCA     180
```

```
CCTAAAGTTT CTTCAGGGGC TTCTAGAAAT AAGATATGTT TTCCTTCTCA ACATAGTACT      240

GGACTGAAGT TTGGATCTCA GGAACGGTCT TGGGATATTT CTTCCACCCC AAAATCAAGA      300

GTTAGAAAAG ATGAAAGGAT GAAGCACAGT TCAGCTATTT CCGCTGTTTT GACCGATGAC      360

AATTCGACAA TGGCACCCCT AGAGGAAGAT GTCAAGACTG AAAATATTGG CCTCCTAAAT      420

TTGGATCCAA CTTTGGAACC TTATCTAGAT CACTTCAGAC ACAGAATGAA GAGATATGTG      480
```

(2) INFORMATION FOR SEQ ID NO:6:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Glu Ile Asn Phe Lys Val Leu Ser Lys Pro Ile Arg Gly Ser Phe
 1               5                  10                  15

Pro Ser Phe Ser Pro Lys Val Ser Ser Gly Ala Ser Arg Asn Lys Ile
            20                  25                  30

Cys Phe Pro Ser Gln His Ser Thr Gly Leu Lys Phe Gly Ser Gln Glu
        35                  40                  45

Arg Ser Trp Asp Ile Ser Ser Thr Pro Lys Ser Arg Val Arg Lys Asp
    50                  55                  60

Glu Arg Met Lys His Ser Ser Ala Ile Ser Ala Val Leu Thr Asp Asp
65                  70                  75                  80

Asn Ser Thr Met Ala Pro Leu Glu Glu Asp Val Lys Thr Glu Asn Ile
                85                  90                  95

Gly Leu Leu Asn Leu Asp Pro Thr Leu Glu Pro Tyr Leu Asp His Phe
            100                 105                 110

Arg His Arg Met Lys Arg Tyr Val
        115                 120
```

(2) INFORMATION FOR SEQ ID NO:7:

(i) SEQUENCE CHARACTERISTICS:
        (A) LENGTH: 1047 base pairs
        (B) TYPE: nucleic acid
        (C) STRANDEDNESS: double
        (D) TOPOLOGY: linear (ii) MOLECULE TYPE: Genomic DNA (ix) FEATURE:
        (A) NAME/KEY: Other
        (B) LOCATION: 1...1047
        (D) OTHER INFORMATION: Tuber specific class 1 pr
           omoter (xi) SEQUENCE DESCRIPTION: SEQ ID NO:7:

```
TTGTTAGTTA ATGCGTATTA GTTTTAGCGA CGAAGCACTA AATCGTCTTT GTATACTTTC       60

AGTGACACAT GTTTAGTGAC GACTGATTGA CGAAATTTTT TTCGTCTCAC AAAATTTTTA      120

GTGACGAAAC ATGATTTATA GATGACGAAA TTATTTGTCC CTCATAATCT AATTTGTTGT      180

AGTGATCATT ACTCCTTTGT TTGTTTTATT TGTCATGTTA GTTCATTAAA AAAAAAATCT      240

CTCTTCTTAT CAATTCTGAC GTGTTTAATA TCATAAGATT AAAAAATATT TTAATATATC      300

TTTAATTTAA AGCCACAAAA TTTAAATTTC TTCGTTAACA TAATTTGTCA AATCAGGCTC      360
```

```
AAAGATCGTT TTTCATATCG GAATCAGGAT TTTATTTATT CTTTTAAAAA TAAAGAGGTG    420

GTGAGCTAAA CAATTTCAAA TCTCATCACA CATATGGGGT CAGCCACAAA AATAAAGAAC    480

GGTTGGAACG GATCTATTAT ATAATACTAA TAAAGAATAG AAAAAGGAAA GTGAGTGAGG    540

TGCGAGGGAG AGAATCTGTT TAATATGCAG AGTCGATCAT GTGTCAGTTT TATCGATATG    600

ACTCTGATTT CAACTGAGTT TAAGCAATTC TGATAAGGCG AGGAAAATCA CAGTGCTGAA    660

ATCTAGAAAA ATCTCATACA GTGAGATAAA TCTCAACAAA AACGTTGAGT CCATAGAGGG    720

GGTGTATGTG ACACCCAACC TCAGCAAAAG AAAACCTCCC CTCAAGAAGG ACATTTGCGG    780

TGCTAAACAA TTTCAAGTCT CATCACACAT ATATATTATA TAATACTAAT AAAGAATAGA    840

AAAAGGAAAG GTAAACATCA CTAATGACAG TTGCGGTGCA AAGTGAGTGA GATAATAAAC    900

ATCAGTAATA GACATCACTA ACTTTTATTG GTTATGTCTT TCTCAAAATA AAATTTCTCA    960

ACTTGTTTAC GTGCCTATAT ATACCATGCT TGTTATATGC TCAAAGCACC AACAAAATTT   1020

AAAAACACTT TGAACATTTG CCCCGGG                                       1047
```

(2) INFORMATION FOR SEQ ID NO:8:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...120
        (D) OTHER INFORMATION: N-terminal sequence rubisco
           activase-AGP small subunit fusion enzyme (xi) SEQUENCE DESCRIPTION: SEQ ID NO:8:

```
Met Ala Thr Ala Val Ser Thr Val Gly Ala Ala Thr Arg Ala Pro Leu
  1               5                  10                  15

Asn Leu Asn Gly Ser Ser Ala Gly Ala Ser Val Pro Thr Ser Gly Phe
             20                  25                  30

Leu Gly Ser Ser Leu Lys Lys His Thr Asn Val Arg Phe Pro Ser Ser
         35                  40                  45

Ser Arg Thr Thr Ser Met Thr Val Lys Ala Ala Glu Asn Glu Glu Lys
     50                  55                  60

Asn Thr Asp Lys Trp Ala His Leu Ala Lys Asp Phe Ser Asp Asp Gln
 65                  70                  75                  80

Leu Asp Ile Arg Arg Gly Lys Gly Met Val Asp Ser Leu Gly Ser Met
                 85                  90                  95

Asp Val Pro Leu Ala Ser Lys Val Pro Leu Pro Ser Pro Ser Lys His
                100                 105                 110

Glu Gln Cys Asn Val Tyr Ser His
            115                 120
```

(2) INFORMATION FOR SEQ ID NO:9:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (ix) FEATURE:

(A) NAME/KEY: Other
(B) LOCATION: 1...120
(D) OTHER INFORMATION: N-terminal sequence of rubisco
    activase-AGP large subunit fusion enz (xi) SEQUENCE DESCRIPTION: SEQ ID NO:9:

Met Ala Thr Ala Val Ser Thr Val Gly Ala Ala Thr Arg Ala Pro Leu
1               5                   10                  15

Asn Leu Asn Gly Ser Ser Ala Gly Ala Ser Val Pro Thr Ser Gly Phe
            20                  25                  30

Leu Gly Ser Ser Leu Lys Lys His Thr Asn Val Arg Phe Pro Ser Ser
        35                  40                  45

Ser Arg Thr Thr Ser Met Thr Val Lys Ala Ala Glu Asn Glu Glu Lys
    50                  55                  60

Asn Thr Asp Lys Trp Ala His Leu Ala Lys Asp Phe Ser Asp Asp Gln
65                  70                  75                  80

Leu Asp Ile Arg Arg Gly Lys Gly Met Val Asp Ser Leu Gly Ile His
                85                  90                  95

Met Gln Phe Ser Ser Val Leu Pro Leu Gly Lys Ala Cys Val Ser
            100                 105                 110

Pro Val Arg Arg Glu Gly Ser Ala
        115                 120

(2) INFORMATION FOR SEQ ID NO:10:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...120
        (D) OTHER INFORMATION: N-terminal sequence of starch
            branching enz - large subunit fusion enz (xi) SEQUENCE DESCRIPTION: SEQ ID NO:10:

Met Glu Ile Asn Phe Lys Val Leu Ser Lys Pro Ile Arg Gly Ser Phe
1               5                   10                  15

Pro Ser Phe Ser Pro Lys Val Ser Ser Gly Ala Ser Arg Asn Lys Ile
            20                  25                  30

Cys Phe Pro Ser Gln His Ser Thr Gly Leu Lys Phe Gly Ser Gln Glu
        35                  40                  45

Arg Ser Trp Asp Ile Ser Ser Thr Pro Lys Ser Arg Val Arg Lys Asp
    50                  55                  60

Glu Arg Met Lys His Ser Ser Ala Ile Ser Ala Val Leu Thr Asp Asp
65                  70                  75                  80

Asn Ser Thr Met Ala Pro Leu Glu Glu Asp Val Lys Thr Glu Asn Ile
            85                  90                  95

Gly Leu Leu Asn Leu Asp Pro Met Gln Phe Ser Ser Val Leu Pro Leu
            100                 105                 110

Glu Gly Lys Ala Cys Val Ser Pro
        115                 120

(2) INFORMATION FOR SEQ ID NO:11:

(i) SEQUENCE CHARACTERISTICS:
        (A) LENGTH: 26 base pairs

```
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

CGGGATCCAT GGATGTACCT TTGGCA                                            26

(2) INFORMATION FOR SEQ ID NO:12:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

CGGGATCCTT ATTTATTTAT ATGACTGTTC CACTAG                                 36

(2) INFORMATION FOR SEQ ID NO:13:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

GCGGATCCAT ATCGAGTTCA GCGT                                              24

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

CGGGATCCGC ACAGGTTGTC GCAGAAC                                           27

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

CGGGATCCGA TGCAGTTCAG CAGCGTG                                           27
```

TRANSGENIC PLANTS OR ALGAE EXPRESSING AN AGP ENZYME COUPLED TO A TRANSIT PEPTIDE

RELATED APPLICATIONS

The present application is a continuation of U.S. patent application Ser. No. 08/535,276, filed Feb. 5, 1996, now U.S. Pat. No. 5,977,437, the disclosure of which is incorporated by reference herein in its entirety, which was a U.S. national phase application of International Application No. PCT/EP94/01082, filed Apr. 7, 1994, the disclosure of which is incorporated by reference herein in its entirety, which claims priority from British Application No. 9307408.6, filed Apr. 8, 1993, the disclosure of which is incorporated by reference herein in its entirety.

FIELD OF THE INVENTION

The present invention relates to a transgenic organism.

In particular, the present invention relates to a transgenic starch producing organism having an increased ability to synthesize starch and one that is capable of producing starch in high yields. More particularly the present invention relates to a transgenic organism comprising a nucleotide sequence coding for exogenous ADP glucose pyrophosphorylase (AGP).

In a preferred embodiment the present invention relates to a transgenic plant or plant cell capable of expressing exogenous AGP in the starch producing centres in the plant, namely the chloroplasts and the amyloplasts. The invention also relates to a recombinant DNA construct for use in the transformation of a plants or plant cell showing enhanced starch production, and plants and plant cells transformed with the recombinant DNA construct.

ADP glucose pyrophosphorylase (E.C.2.7.7.27) (AGP) is one of the primary enzymes involved in the biosynthesis of starch and glycogen in organisms such as plants, algae, fungi and bacteria, particularly plants.

AGP catalyses the reaction:

the product ADP-glucose being the major donor of glucose in the biosynthesis of starch in plants. Moreover, that reaction has been shown to be the rate limiting factor in the synthesis of starch in organisms such as plants, the rate of that reaction in turn being critically dependent upon the AGP concentration. Because of that, AGP has been the subject of intensive investigation and for a general review of recent studies on plant AGP, reference should be made to Kleczkowski et al: Z. Naturforsch. 46c, 605–612 (1991).

As reported by Kleczkowski et al (ibid) and elsewhere, AGP is widely distributed throughout the plant kingdom and is found in some starch producing bacteria, such as E. coli. Plant AGP exists as a tetramer (210 to 240 kDa) composed of two small sub-units (50 to 55 kDa) and two large sub-units (51 to 60 kDa) in contrast to bacterial AGP which appears to consist of four units of equal size. AGP has also been shown to be produced in cyanobacteria and in algae, where its tetrameric structure is similar to that in plants, i.e. two large and two small sub-units, rather than the homotetrameric structure found in ordinary bacteria.

Because of the commercial importance of starch, primarily as a foodstuff but also as an important industrial chemical, AGP itself and recombinant DNA constructs containing DNA sequences encoding AGP for the transfection of plants and plant cells as a means of increasing plant AGP concentration and hence increased biosynthesis of starch in plants and increased starch yields, have formed the subject matter of several recently published patent applications.

For example, in EP-A-0368506 a method of extracting AGP from wheat leaf and wheat endosperm is disclosed. Also disclosed are the cDNA sequences encoding wheat leaf and wheat endosperm AGP, and various plasmids containing those sequences for subsequent insertion into plants to provide plants having an increased ability to synthesise starch, although that latter step is not described in detail, nor are any examples given of transgenic plants containing those constructs.

WO 91/19806 discloses transformed plant cells and plants having elevated levels of starch and starch biosynthesis achieved by incorporating into the plant genome a DNA construct comprising in sequence a plant promoter, a DNA sequence encoding a fusion polypeptide consisting of a plastid transit peptide and a bacterial (E. coli) AGP, and a 3'-non-translated region which functions in the plant cell to cause transcriptional termination and the addition of a polyadenylated tail to the 3'-end of the corresponding DNA sequence. The DNA sequence encoding E. coli AGP is given, as well as the deduced amino acid sequence. Transgenic potato and tomato plants transformed with the E. coli AGP gene are shown to produce increased starch yields. It is suggested that other bacterial sources besides E. coli, and also algae, may be used as a source for the AGP gene to be used in the transformation of the plants and plant cells to provide increased starch yields. However, there is no mention of the isolation of nucleotide sequences coding for AGP enzymes from those other sources or their expression in such transgenic systems.

A similar disclosure is contained in WO 92/11382 which likewise discloses the transformation of plants, especially potato plants, with bacterial (E. coli) DNA encoding bacterial AGP, with the objective of increasing starch biosynthesis and starch yield in such plants.

A slightly different objective is set out in EP-A-0455316. There the objective is to increase sugar and protein concentrations in plant-based foodstuffs at the expense of starch formation. That is achieved by incorporating into the plant genome a DNA sequence encoding AGP, but in an inverted orientation in the transformation vector. Transcription of the reversed sequence results in an anti-sense mRNA which inhibits the production of AGP in the plant cell leading to reduced AGP activity and reduced starch production.

All plant AGPs investigated so far have been reported to be strongly activated by 3-phospho-glycerate (PGA) and inhibited by inorganic phosphate ($P_i$). Also, the PGA/$P_i$ ratio in the chloroplasts and amyloplasts where biosynthetic starch production is concentrated is believed to play a key regulatory role in starch synthesis. It is known, for example, that chloroplast PGA/$P_i$ ratios are at the highest activity during the daylight hours, i.e. during photosynthesis, which period coincides with the peak period of starch production in the chloroplasts. The regulation of the AGP formation in non-photosynthetic tissues is less well understood, but the activatory and inhibitory roles of PGA and $P_i$, respectively, i.e. the PGA/$P_i$ ratio, is believed still to play an important part.

SUMMARY OF THE INVENTION

The present invention addresses the problem of how to increase AGPase levels and/or starch levels in starch producing organisms.

According to a first aspect of the present invention there is provided a transgenic starch producing organism comprising a nucleotide sequence coding for an exogenous ADP glucose pyrophosphorylase (AGP) enzyme or a sub-unit thereof which retains the enzymatic activity of the AGP enzyme, wherein the nucleotide sequence is capable of being expressed in the organism; characterised in that the activity of the enzyme or sub-unit thereof is substantially independent of any level of in vivo 3-phospho-glycerate and/or any in vivo level of inorganic phosphate; and further characterised in that the activity of the enzyme or sub-unit thereof is not stimulated by fructose-1,6bisP and/or is not inhibited by AMP.

According to a second aspect of the present invention there is provided a transgenic starch producing organism comprising exogenous ADP glucose pyrophosphorylase (AGP) enzyme or a sub-unit thereof which retains the enzymatic activity of the AGP enzyme, wherein the activity of the enzyme or sub-unit thereof is substantially independent of any level of in vivo 3-phospho-glycerate and/or any in vivo level of inorganic phosphate and wherein the activity of the enzyme or sub-unit thereof is not stimulated by fructose-1,6-bisP and/or is not inhibited by AMP.

According to a third aspect of the present invention there is provided a potato tuber containing an enhanced starch content.

According to a fourth aspect of the present invention there is provided a method of increasing the rate and/or yield of starch production in an organism, especially a plant or a plant cell, which method comprises introducing into an organism a nucleotide sequence according to the present invention to form a transgenic organism according to the present invention and expressing the nucleotide sequence.

According to a fifth aspect of the present invention there is provided a method of increasing the rate and/or yield of starch production in an organism, especially a plant or a plant cell, which method comprises introducing into or forming in an organism a ADP glucose pyrophosphorylase (AGP) enzyme or a sub-unit thereof according to the present invention.

According to a sixth aspect of the present invention there is provided any one of the following: A cDNA sequence identified herein as SEQ ID No. 2, including noncritical allelic variations of that sequence; An amino acid sequence as shown in SEQ ID No. 4, including variants thereof having non-critical amino acid substitution(s) or deletion(s) at one or more locations in that sequence; A cDNA sequence identified herein as SEQ ID No. 5 including non-critical allelic variations of that sequence; An amino acid sequence as shown in SEQ ID No. 6, including variants thereof having non-critical amino acid substitution(s) or deletion(s) at one or more locations in that sequence.

According to a seventh aspect of the present invention there is provided any one of the following plasmids: Plasmid pPPS1; Plasmid pPPL1; Plasmid pPPL1M; Plasmid pPPS4; Plasmid pPPL4; Plasmid pPPL5; Plasmid pBKL4; Plasmid pVictor IV GN.

According to an eighth aspect of the present invention there is provided a method of increasing the rate and/or yield of starch production in an organism, especially a plant or a plant cell, which method comprises introducing into an organism a recombinant DNA construct containing an exogenous DNA sequence encoding an exogenous ADP glucose pyrophosphorylase enzyme (AGP) or sub-unit thereof and one or more promoter sequences enabling the expression of the AGP encoded by that sequence by the organism thereby to increase the AGP content of the organism and in consequence to increase the rate of starch production by the organism and/or the starch yield, characterised in that the said DNA sequence is the gene sequence encoding the barley (*Hordeum vulgare*) endosperm AGP or a sub-unit thereof, or a variant thereof having non-critical amino acid substitution(s) or deletion(s) at one or more points in the amino acid sequences defining the barley endosperm AGP or either of its sub-units, wherein the construct is expressed in the organism; characterised in that the activity of the enzyme or sub-unit thereof is substantially independent of any level of in vivo 3-phospho-glycerate and/or any in vivo level of inorganic phosphate; and further characterised in that the activity of the enzyme or sub-unit thereof is not stimulated by fructose-1,6-bisP and/or is not inhibited by AMP.

According to a ninth aspect of the present invention there is provided a vector for the transformation of an organism, especially a plant or a plant cell, to increase the AGP content of such an organism consequently to increase the rate of starch production by such an organism, such vector comprising a recombinant DNA construct containing a DNA sequence encoding an exogenous ADP glucose pyrophosphorylase enzyme (AGP), such vector also incorporating the necessary promoter and other sequences enabling the expression of that exogenous AGP in an organism transformed by that vector, characterised in that the said DNA sequence is the gene sequence encoding the barley (*Hordeum vulgare*) endosperm AGP or a sub-unit thereof, or a variant thereof having non-critical amino acid substitution (s) or deletion(s) at one or more points in the amino acid sequences defining the barley endosperm AGP or either of its sub-units, wherein the construct is capable of being expressed in the organism; characterised in that the activity of the enzyme or sub-unit thereof is substantially independent of any level of in vivo 3-phospho-glycerate and/or any in vivo level of inorganic phosphate; and further characterised in that the activity of the enzyme or sub-unit thereof is not stimulated by fructose-1,6-bisP and/or is not inhibited by AMP.

According to a tenth aspect of the present invention there is provided a method of targeting an exogenous protein to the amyloplast of plants or plant cells which comprises introducing into the plant or plant cell a recombinant DNA construct containing a DNA sequence encoding a starch branching enzyme transit peptide and an exogenous DNA sequence encoding the exogenous protein; wherein the construct is capable of being expressed in the plant or plant cells; preferably wherein the DNA sequence encoding the starch branching enzyme comprises the sequence identified as SEQ ID No.5 and/or the starch branching enzyme expressed in the plant or plant cell by said construct comprises the amino acid sequence identified as SEQ ID No.6.

According to an eleventh aspect of the present invention there is provided an AGP enzyme or sub-unit thereof whose in vivo activity is substantially independent of any level of in vivo 3-phospho-glycerate and/or any in vivo level of $P_i$, and whose activity is not stimulated by fructose-1,6-bisP and/or is not inhibited by AMP.

According to a twelfth aspect of the present invention there is provided a foodstuff made from or comprising an organism according to the present invention; preferably wherein the foodstuff is a fried foodstuff; more preferably wherein the foodstuff is a potato.

The term 'transgenic organism' in relation to the present invention means an organism comprising an expressable exogeneous nucleotide sequence or an expressed product of such an expressable exogeneous nucleotide sequence. Preferably the expressable exogeneous nucleotide sequence is incorporated in the genome of the organism.

The term 'organism' in relation to the present invention includes any starch producing organisms such as plants, algae, fungi and bacteria, as well as cells thereof. Preferably the term means a plant or cell thereof, more preferably a potato and especially a potato tuber.

The term 'nucleotide' in relation to the present invention includes genomic DNA, cDNA, synthetic DNA, and RNA. Preferably it means DNA, more preferably cDNA.

The terms 'allele' and 'variant' in relation to the present invention mean any substitution of, variation of, modification of, replacement of, deletion of or the addition of one or more nucleic acid(s)/amino acids from or to the sequence providing the resultant sequence expresses or exhibits the required enzymatic activity. They also mean a substantial homologous sequence wherein there is homology with respect to at least the essential nucleic acids/nucleic acid residues/amino acids for expression of or exhibition of the required enzymatic activity. Preferably there is at least 80% homology, more preferably at least 90% homology, and even more preferably there is at least 95% homology with the listed sequences. Hybrid sequences are also covered. These may be prepared from at least two different sources—e.g. the variant may include a sequence from one source that gives the variant the independence vis-a-vis the level of in vivo 3-phospho-glycerate and a sequence from another source that gives the variant the independence vis-a-vis the level of in vivo $P_i$.

The term 'sub-unit' in relation to the present invention means an active component of the enzyme that displays the required enzymatic activity. For example, in the case of AGP enzyme obtained from barley (*Hordeum vulgare*), which is a heterotetramer containing two large sub-units and two small sub-units, the term includes any one of those sub-units as well as combinations thereof as well as a shortened variant thereof.

The term 'retains enzymatic activity' in relation to the present invention means that the activity of the enzyme variant or sub-unit thereof is still substantially independent of any level of in vivo 3-phospho-glycerate and/or any in vivo level of inorganic phosphate, but not necessarily to the same extent as the native enzyme.

The term 'substantially independent' in relation to the present invention means that the enzyme has a decreased sensitivity to levels of PGA and/or of inorganic phosphate, preferably at least to PGA. By way of example, in the absence of PGA the levels of AGPase activity of the native enzyme or sub-unit thereof are in the order of at least 0.002 units per mg protein, preferably at least 0.01 units per mg protein—when measured in Bintje potato tuber extract. Typically, in the case of the preferred barley AGP enzyme we have found that the AGPase levels of the large sub-unit are greater than the levels of the small sub-unit and are typically in the order of greater than 0.02 units per mg protein and can be in the order of 0.05 units per mg protein—when measured in Bintje potato tuber extract. This is in contrast to the known enzymes which have no, or at most negligible, AGPase activity in the absence of PGA.

Preferably the enzymatic activity of the AGP enzyme is at least substantially independent of any level of in vivo 3-phospho-glycerate.

More preferably the enzymatic activity of the AGP enzyme is not stimulated by fructose-1,6-bisP and it is not inhibited by AMP.

Preferably the AGP enzyme is a heteromer, preferably a heterotetramer, more preferably a heteromer containing two large sub-units and two small sub-units.

Preferably the AGP enzyme is isolatable from Hordeum, preferably wherein the enzyme is barley (*Hordeum vulgar*) endosperm AGP or a sub-unit thereof, or a variant thereof having non-critical amino acid substitution(s) or deletion(s) at one or more points in the amino acid sequences defining the barley endosperm AGP or either of its sub-units.

Preferably the nucleotide sequence is a DNA sequence.

Preferably the DNA sequence encodes the large sub-unit of the barley endosperm AGP or a variant thereof having non-critical amino acid substitution(s) or deletion(s) at one or more points in the amino acid sequence defining the large sub-unit of the barley endosperm AGP.

Preferably the DNA sequence is the sequence identified herein as SEQ ID No. 1, including non-critical allelic variations of that sequence.

Preferably the DNA sequence encodes the small sub-unit of the barley endosperm AGP, or a variant thereof having non-critical amino acid substitution(s) or deletion(s) at one or more points in the amino acid sequence defining the small sub-unit of the barley endosperm AGP.

Preferably the DNA sequence is the sequence identified herein as SEQ ID No. 2, including non-critical allelic variations of that sequence.

Preferably both of the DNA sequences are expressed in the same organism. The DNA sequences need not be derived from the same initial source, such as barley. It is preferred however that they are from the same source, for example barley.

Preferably, when both of the DNA sequences are expressed in the same organism, each DNA sequence additionally codes for a different marker—e.g. the large or small sub-unit of barley AGP enzyme may be in a construct that contains a kanamycin resistance gene such as a construct based on plasmid pBKL4 or pVictor IV GN and another small or large sub-unit of barley AGP enzyme may be in a construct that contains a mannose isomerase gene such as a construct based on plasmid pVictor IV SGiN Man.

Preferably the expressed AGP enzyme or sub-unit thereof comprises the amino acid sequence set out in SEQ ID No. 3, or a variant thereof having non-critical amino acid substitution(s) or deletion(s) at one or more locations in that sequence.

Preferably the expressed AGP enzyme or sub-unit thereof comprises the amino acid sequence set out in SEQ ID No. 4, or a variant thereof having non-critical amino acid substitution(s) or deletion(s) at one or more locations in that sequence.

Preferably the expressed ACP comprises both a large sub-unit having the amino acid sequence set out in SEQ ID No. 3 or a variant thereof having non-critical amino acid substitution(s) or deletion(s) at one or more locations in that sequence, and a small sub-unit having the amino acid sequence set out in SEQ ID No. 4 or a variant thereof having non-critical amino acid substitution(s) or deletion(s) at one or more locations in that sequence.

Preferably the nucleotide sequence additionally codes for a transit peptide which can transport, or assist in the transportation of, the enzyme or sub-unit thereof from the cytoplasm to the relevant or appropriate plastid(s), such as a chloroplast and/or an amyloplast. Preferably the transit peptide is Rubisco Activase transit peptide or Starch Branching enzyme transit peptide.

Preferably the transit peptide is coded for by a DNA sequence comprising the sequence identified as SEQ ID No. 5, including non-critical allelic variations of that sequence.

Preferably the transit peptide has an amino acid sequence comprising the sequence identified as SEQ ID No 6, or a variant thereof having non-critical amino acid substitution(s) or deletion(s) at one or more locations in that sequence.

Preferably the nucleotide sequence is operatively connected to a promoter which expresses the sequence wherein the promoter is cell, tissue or organ specific.

Preferably the promoter has the sequence identified as SEQ ID No. 7, or a variant thereof having non-critical nucleotide substitution(s) or deletion(s) at one or more locations in that sequence.

Preferably the AGP enzyme or sub-unit thereof comprises the amino acid sequence set out in SEQ ID No. 3, or a variant thereof having non-critical amino acid substitution(s) or deletion(s) at one or more locations in that sequence and/or the amino acid sequence set out in SEQ ID No. 4, or a variant thereof having non-critical amino acid substitution(s) or deletion(s) at one or more locations in that sequence.

Preferably the organism is a transgenic plant.

Preferably the transgenic plant is a potato plant.

Preferably the nucleotide sequence according to the present invention is obtainable from any one of the following plasmids: Plasmid pVictor IV SGiN Man; Plasmid pPPS 1; Plasmid pPPL1; Plasmid pPPL1M; Plasmid pPPS4; Plasmid pPPL4; Plasmid pPPL5; Plasmid pBKL4; Plasmid pVictor IV GN.

Preferably the enzyme is obtainable from a eukaryotic source.

The present invention has broad applicability to starch producing organisms, especially plants. The present invention works better in organisms such as plants compared to bacteria.

In particular the present invention works better in plants compared to $E.\ coli$ where AGP activity is stimulated by fructose-1,6-bisP and inhibited by AMP. This $E.\ coli$ pathway is different to the pathway for the biosynthesis of starch in plants and algae.

With regard to one preferred aspect of the present invention, namely a foodstuff prepared from frying a potato according to the present invention, it is to be noted that the increased starch content of the potato will lead to less fat/oil uptake during frying This results in obvious dietary advantages. Moreover, the increased levels of starch also means that there are decreased free levels of reducing carbohydrates—which are used in starch synthesis—and so there is a decreased tendancy for the resultant product to become discoloured on frying by example reaction of the reducing carbohydrates with the hot fat/oil.

In accordance with a preferred aspect of the present invention it was found that AGP from barley (*Hordeum vulgare*) endosperm is highly active even in the absence of the activator PGA and is relatively insensitive to PGA/P; ratios which play an important regulatory function in the case of AGP from most other known plant sources. The PGA/$P_i$; ratio is also believed to play an important regulatory function in non-plant AGP, e.g. algal AGP.

The cDNA sequences encoding parts of the large and the small sub-units of the barley endosperm AGP and the deduced amino acid sequences have recently been established and published in Plant Molecular Biology, 19, 381–389 (1992). The complete DNA sequence encoding the large sub-unit together with the cDNA for the large sub-unit are set out in Plant Physiol. 100 1617–1618, (1992).

In accordance with the present invention the complete DNA sequence encoding the small sub-unit of the barley endosperm AGP and the deduced amino acid sequence has now been established. Those complete cDNA sequences are reproduced herein as SEQ ID Nos. 1 and 2 encoding, respectively, the large and small sub-units of the barley endosperm AGP, whilst the deduced amino acid sequences are set out herein as SEQ ID Nos. 3 and 4, respectively.

Thus, in the preferred embodiment of the present invention, it was discovered that starch production in plants can be enhanced/increased by incorporating into the plant's genome and under the control of suitable promoter sequence or sequences promoting the expression of the gene in the plant cells, particularly in the chloroplasts and amyloplasts, DNA sequences encoding either the large (60 kDa) sub-unit of barley (*Hordeum vulgare*) endosperm AGP or the small (51 kDa) unit, or both.

Thus, in a highly preferred aspect of the present invention there is provided transgenic plants and plant cells having increased rates of starch production and/or starch content, as compared with the corresponding non-transformed plant or plant cell, such plants and plant cells having been transformed with a recombinant DNA construct containing, in operational relationship (particularly in downstream relationship) to a plant promoter sequence or sequences enabling the expression of the gene in the plant or plant cell, the gene sequence encoding the barley (*Hordeum vulgare*) endosperm AGP or an active sub-unit thereof retaining the enzymatic activity of the heterotetrameric AGP, or a variant thereof having non-critical amino acid substitution(s) or deletion(s) at one or more locations in the amino acid sequences defining the barley endosperm AGP or either of its sub-units.

Whilst, in accordance with the present invention, a wide variety of organisms (e.g. plants and plant cells) may be transformed (especially with the gene encoding barley endosperm AGP or either of its sub-units) to increase starch production and starch yields in that particular organism, the preferred embodiment concerns the transformation of the major starch producing plant crops, namely potato, rice, wheat and maize, which four crops in terms of calorific value, probably account for three quarters of the world's food supply. Sugar beet may also be transformed.

In a more specific aspect of the present invention there are provided transgenic plants and plant cells having increased rates of starch production and/or providing increased starch yields compared with the non-transformed material, such plants and plant cells having been transformed with a recombinant DNA construct containing in downstream relationship to a plant promoter sequence or sequences enabling the expression of the gene in the transformed plant or plant cells, either or both the sequences SEQ ID No. 1 and SEQ ID No. 2 as set out in the prescribed fashion in the sequence listings annexed hereto and which are taken to be part of the present specification, or an allelic variant of either sequence showing substantial homology with the listed sequence and containing non-critical nucleotide substitutions at one or more locations in the nucleotide chain.

Alternatively defined, there are provided, in accordance with the present invention, transgenic plants and plant cells showing enhanced levels of AGP production, particularly, in the chloroplasts and amyloplasts, such plants and plant cells having been transformed with a recombinant DNA construct enabling the expression within the plant or plant cells of barley endosperm AGP or either of its sub-units, those sub-units having the derived amino acid sequences set out in SEQ ID Nos. 3 and 4, or a variant of such a sequence having non-critical amino acid substitution(s) or deletion(s) at one or more locations in the amino acid sequence defining the barley endosperm AGP or either of its sub-units.

Also provided in accordance with this invention are plant transformation vectors for the transformation of plants and plant cells to increase the AGP content of such plants and plant cells and thus to increase the rate of production of starch by the transformed plant or plant cell and/or the starch yield, such vectors containing one or more promoter sequences functional in plants linked in operational relationship with a DNA sequence encoding barley endosperm AGP, or either of its sub-units. More especially plant transformation vectors are provided comprising one or more promoter sequences functional in plants linked in operational relationship with either or both the sequences SEQ ID No. 1 or SEQ ID No. 2, or an allelic variant of either sequence showing substantial (at least 80%) homology with the listed sequence but having non-critical nucleotide substitution(s) at one or more locations in the nucleotide chain.

With regard to the promoter, numerous promoters which are functional in plants are known. The promoter should be capable of allowing sufficient expression to result in the desired increase in starch production. Preferably, the promoter should be chosen so that the increased starch production is carried out in the plant tissues where the starch production is required. For instance the promoters of starch biosynthetic genes from plants may be useful.

Known examples of such promoters include the promoter of the granule bound starch synthase gene from potato (Van der Leij et al. [1991] Mol. Gen. Genet. 228: 240–248), and the promoter of the starch branching enzyme gene Sbe 1 from rice (Kawasaki et al. [1993] Mol. Gen. Genet. 237: 1–16).

For expression in potato, a tuber specific class I patatin promoter is preferred (Mignery et al. [1988] Gene. 62: 27–44). The DNA sequence encoding the tuber specific class I patatin promoter is set out in the appendix hereto as SEQ ID No. 7. This patatin promoter was obtained from Dr. William Belknap, USDA—ARS, Alabany, Calif.

The DNA sequence encoding barley endosperm AGP is preferably linked to other control sequences for the expression of the DNA in addition to a promoter sequence such as a transcription terminator sequence. Transcription terminators may be derived from a variety of different genes, including plant, viral and Agrobacterium genes. A cauliflower mosiac virus 35S terminator is preferred.

AGP activity can occur in different sites in plants. For example in potatoes AGP activity is mainly localised in the chloroplasts (i.e. plastids specialising in photosynthesis) or the amyloplasts (i.e. plastids specialising in starch storage). Many amyloplast-localised proteins are expressed as precursors and are targeted to the amyloplast by an appropriate transit peptide that is subsequnetly removed. Similarly, many chloroplast-localised proteins are expressed as precursors which can be targeted to the chloroplast by an appropriate target peptide.

Whilst not wishing to be bound by any theory, it is believed that both the large and small sub-units of the barley endosperm AGP are synthesised as precursor peptides. Additional sequences are found to be attached to the amino-termini of the mature proteins which are understood to represent transit peptides. The transit peptide is then cleaved upon sequestration of the presursor protein into the plastid. It is understood that the enzyme is not subjected to any other post-translation modification process in vivo.

However, in another embodiment of the present invention, it is desirable for the AGP transit peptides to be supplemented with one or more additional transit peptides. The transit peptide can be conveniently fused directly at the amino terminal methionine of the AGP barley sub-unit. In further preferred embodiments the barley AGP transit peptide can be substituted by another amyloplast or chloroplast transit peptide. The barley endosperm AGP cDNA is inserted into a convenient cloning vector, e.g. a plasmid, at a suitable restriction site. The DNA sequence of interest can be enclosed into further vectors, if necessary, for the incorporation of additional DNA sequences. Suitable plant transit peptides include known chloroplast (Gavel & Von Heine [1990] FEBS Lett. 261: 455–458) or amyloplast (Van der Leij et al. [1991] Mol. Genet. 228: 240–248; Klosgen et al. [1989] Mol. Gen. Genet. 217: 155–161; Brisson et al. The Plant Cell [1989] 1: 559–566) transit peptides.

In potatoes, preferably a rubisco activase transit peptide (Werneke et al. Proc. Natl. Sci. USA [1988] 85: 787–791) or a starch branching enzyme transit peptide is used. The 480 bp starch branching enzyme cDNA sequence from potato showing 120 nucleotides of the $5^1$ untranslated region and 360 nucleotides of the coding region (see SEQ ID No. 5), which contains a putative 75 amino acid transit peptide and 45 amino acids of the mature branching enzyme is set out in the appendix hereto as SEQ ID No. 6.

In addition to the transit peptide portion of a protein, it may be desirable to include sequences encoding a portion of the mature plastid-targeted protein to further facilitate intracellular transport.

Preferably the plasmids are also provided with selection markers to enable the transformed plant cells to be separated out from plant cells which have not been transformed. Suitable genes are known and include e.g. a neomycin phosphotransferase gene (e.g. neo npt II), a phosphinotricine/bialaphos acetyl-tranferase gene (e.g. bar) and a β-glucuronidase gene (e.g. uidA) or a phosphomannose isomerase gene (e.g. manA, pmi).

In a preferred embodiment, the transformation vectors may be prepared by initially obtaining cDNA encoding the small and large units of barley endosperm AGP by the method described in Plant Molecular Biology, 19, 381–389 (1992). For ligation into a convenient cloning vector, e.g. a plasmid, the barley endosperm AGP cDNA is provided with restriction sites at each end by PCR using the oligonucleotide primers obtained by conventional oligonucleotide synthesis procedures or a commercially available oligonucleotide synthesizer such as, for example, Applied Biosystems 381 A DNA synthesizer. These restriction sites should be homologous with sequences in the cloning vector. The desired DNA sequence can be recloned into further vectors for preparation of the ultimate transformation vectors for preparing the transgenic starch producing organism, especially a transgenic plant.

In the preferred embodiment of the present invention, the plant or plant cells may be transformed by any suitable technique for transforming cells—such as use of T-DNA, electroporation, injection, DNA bombardment or fusion. After transformation, a whole plant can be cultivated from a transformed plant cell in the usual manner.

Preferably, transformation of the plant cell is achieved with T-DNA using *Agrobacterium tumefaciens* or *Agrobacterium rhizogenes*. If agrobacteria are used for transformation, the barley endosperm cDNA needs to be incorporated initially into either an intermediate vector or a binary vector. The intermediate vectors can be integrated into *Agrobacterium tunefaciens* by means of a helper plasmid. Preferably binary vectors are used, which can be transformed directly into agrobacteria. Binary vectors comprise a selection marker gene and a linker or polylinker which are framed by the right and left T-DNA border regions. The agrobacteria used as host cell should comprise a plasmid carrying a vir region, which is necessary for the transfer of the T-DNA into the plant cell. Transformation using Agrobacterium is achieved by cultivating the Agrobacterium with the plant cell.

Depending on the plant species to be transformed, a variety of different plant transformation vectors can be used. These include pBIN 121, pAL4404, pEHA101, pBKL4, pVictor IV SGiNMan and pVictor IV GN.

For the transformation of potato species Agrobacteria the preferred plant transformation vectors are the plasmids pBKL4, pVictor IV SGiNMan and pVictor IV GN. These plasmids are described later in greater detail.

Preferred plasmids used in the construction of the plasmid used for transformations include pPATA1 and pBluescript II KS. Plasmid pBluescript II KS is a widely used cloning vector available from Stratagene.

Plants can be confirmed as transformed by performing conventional blotting assays and PCR.

The starch content of the plants can be analysed based upon the specific gravity determined using the weight in water and the weight in air as described by W. A. Gould In: Chipping Potato Handbook, ed. Gould, W. A. The Snack Food Association, Vermont, 1989, pp 18–22, in an article entitled "Specific gravity, its measurement and use".

The limitation of the exogenous ADP glucose pyrophosphorylase (AGP) enzyme or a sub-unit thereof which retains the enzymatic activity of the AGP enzyme being not stimulated by fructose-1,6-bisP and/or not inhibited by AMP, which further distinguishes the present invention from the AGP enzymes of the prior art such as those of WO 91/19806 and WO 92/11382, can be expressed in the alternative as either the exogenous ADP glucose pyrophosphorylase (AGP) enzyme or a sub-unit thereof which retains the enzymatic activity of the AGP enzyme not being only just an *E. coli* AGP enzyme, or the exogenous ADP glucose pyrophosphorylase (AGP) enzyme or a sub-unit thereof which retains the enzymatic activity of the AGP enzyme being capable of catalysing the reaction

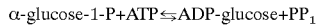

α-glucose-1-P+ATP⇌ADP-glucose+PP$_i$

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on Mar. 29, 1994:

*E. coli* containing plasmid pPPS1 (NCIMB 40618);
*E. coli* containing plasmid pPPL1 (NCIMB 40619);
*E. coli* containing plasmid pPPS4 (NCIMB 40620);
*E. coli* containing plasmid pPPL4 (NCIMB 40621); and
*E. coli* containing plasmid pPPLS (NCIMB 40622).

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on Mar. 31, 1994:

*E. coli* containing plasmid pBKL4 (NCIMB 40623);
*E. coli* containing plasmid pVictor IV GN (NCIMB 40624); and
*E. coli* containing plasmid pVictor IV SGiN Man (NCIMB 40625).

A detailed construction of plant transformation vectors according to the present invention and the transformation of plants and plant cells using those vectors to produce transgenic plants according to this invention having increased rates of starch biosynthesis and/or starch yield will now be described in more detail.

In this regard, the present invention will now be described only by way of example.

BRIEF DESCRIPTION OF THE DRAWINGS

FIG. 8 shows the N terminal amino acid sequence of the rubisco activase—AGP small subunit fusion enzyme (SEQ ID No. 8), the N terminal amino acid sequence of the rubisco activase—AGP large subunit fusion enzyme (SEQ ID No. 9) and the N terminal amino acid sequence of the starch branching enzyme—AGP large subunit fusion enzyme(SEQ ID No. 10)

In the following Examples the following amino acid codes are used:

| Symbol | 3-letter | Meaning |
|---|---|---|
| A | Ala | Alanine |
| B | Asp,Asn | Aspartic Asparagine |
| C | Cys | Cysteine |
| D | Asp | Aspartic |
| E | Glu | Glutamic |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| X | Xxx | Unknown |
| T | Tyr | Tyrosine |
| Z | Glu,Gln | Glutamic Glutamine |
| + | End | Terminator |

DETAILED DESCRIPTION OF THE INVENTION

A. Construction of Plant Transformation Vectors Containing the ADP-alucose Pyrophosphorylase Genes Expressed from a Datatin Class I Promoter

EXAMPLE 1

Plasmid pPPS1

Plasmid pPPS1 is a pBKL4 derivative containing the construction: Patatin promoter—small sub-unit AGP cDNA—35S terminator The AGP cassette was inserted in the KpnI site of pBKL4. The additional elements introduced in the pBKL4 T-DNA by this insertion are descibed below.

Patatin promoter: The patatin promoter is a tuber specific promoter from potato (Mignery et al. 1988, Gene 62:27–44)—see SEQ ID No. 7.

Small subunit ADP-glucose pyrophosphorylase (bepsF2): This is a 1.8 kb cDNA fragment encoding the srnall subunit ADP-glucose pyrophosphorylase from barley endosperm—see SEQ ID No. 2.

35S tenninator: The CaMV 35S terminator (Odell et al. 1985, Nature 313:810–812) is fused to the bepsF2 fragment.

Figure 1:
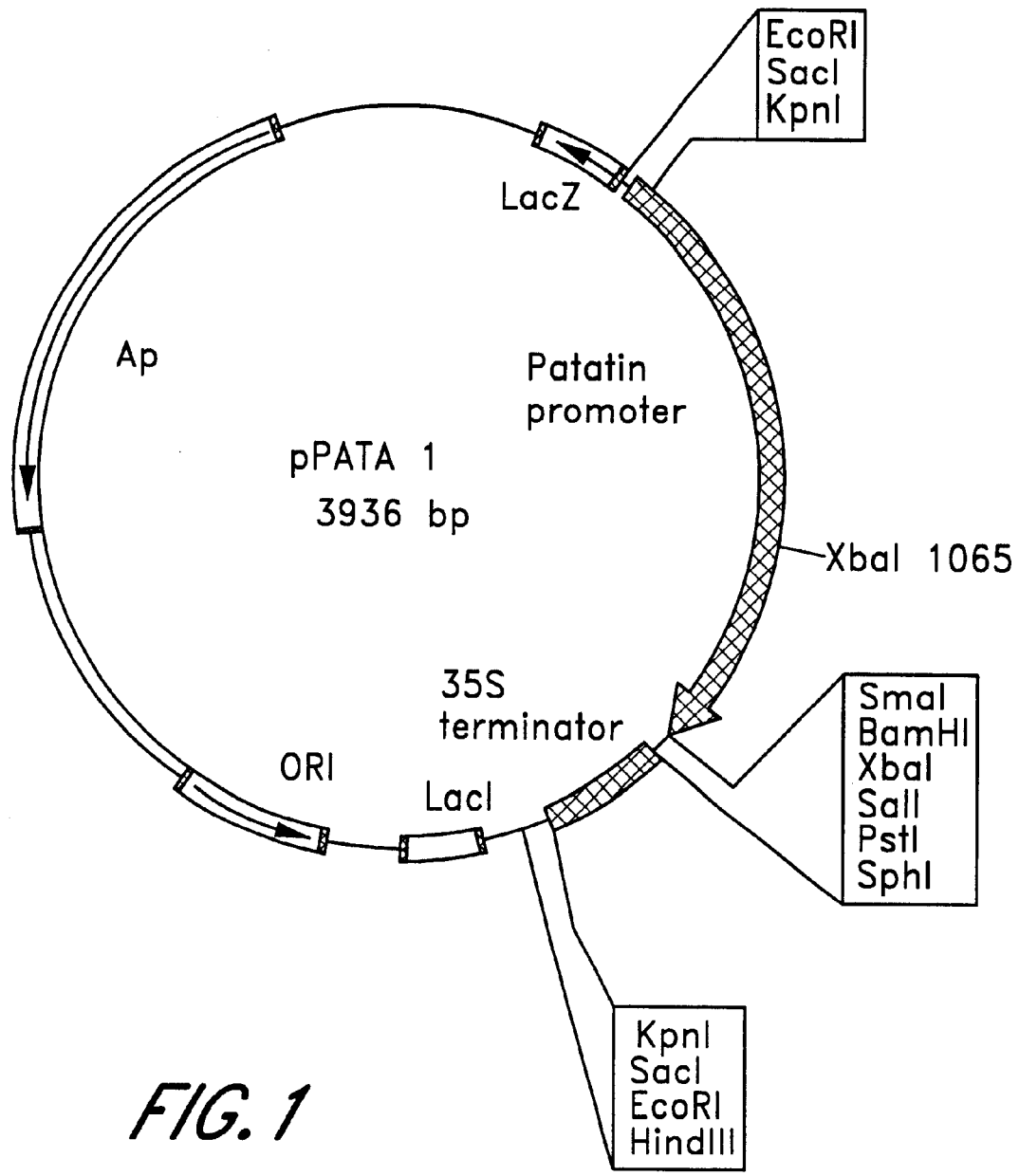
FIG. 1 shows the restriction map for plasmid pPATA1.
Figure 2:
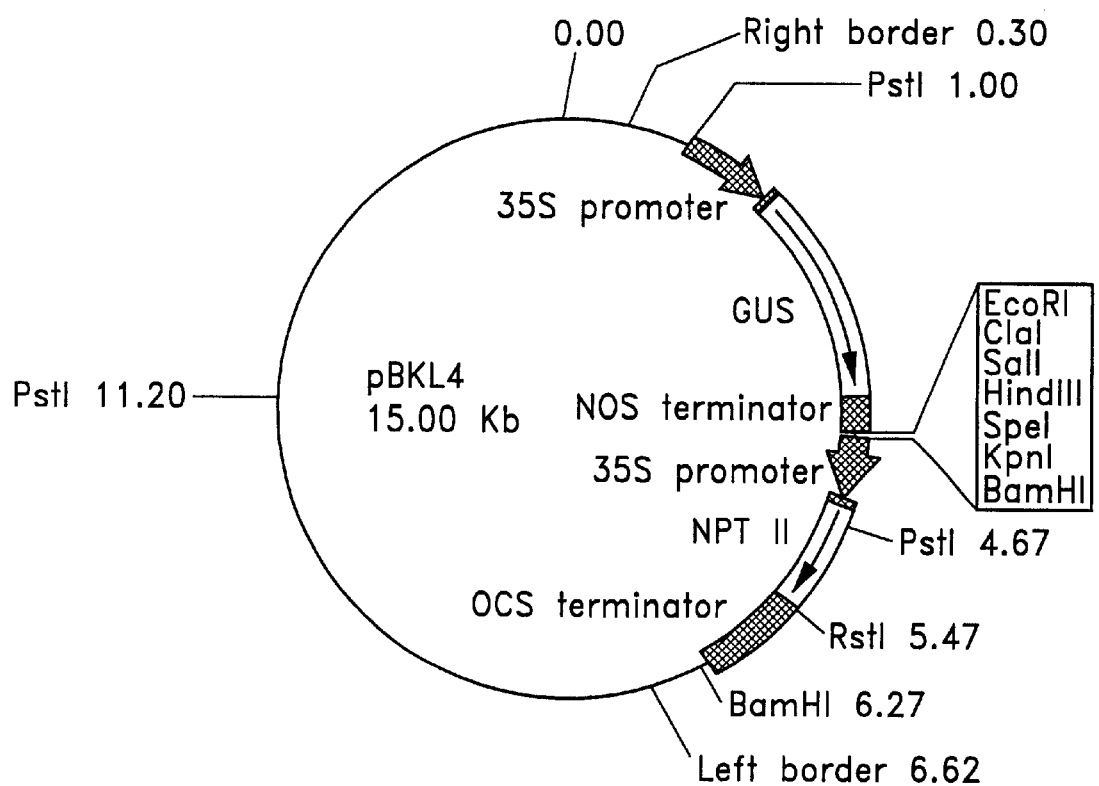
FIG. 2 shows the restriction map for plant transformation vector pBKL4.
Figure 3:
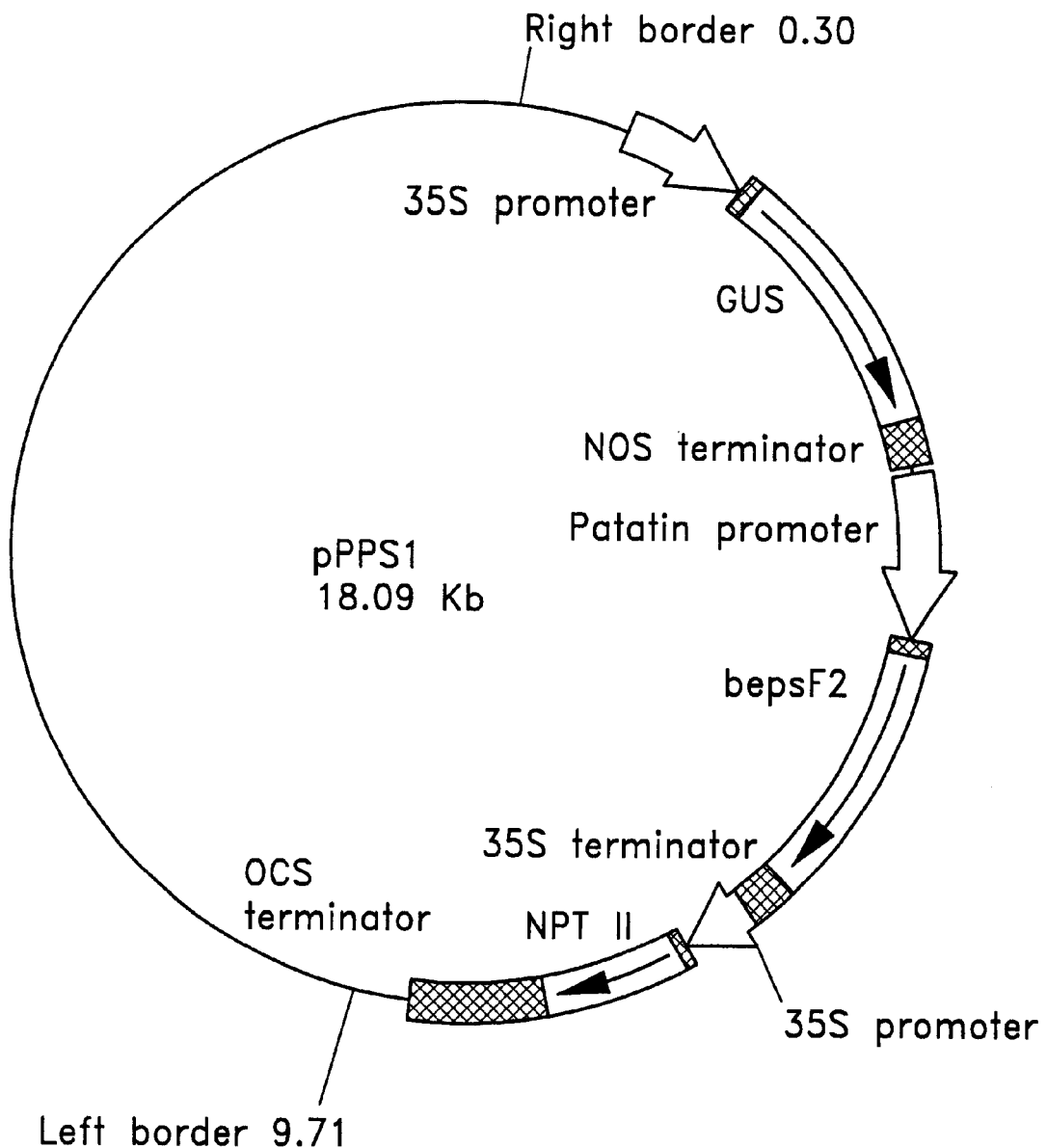
FIG. 3 shows the restriction map for plasmid pPPS1.

In more detail, a 1.8 kb BamHI cDNA fragment encoding the barley endosperm ADP glucose pyrophosphorylase small subunit (beps) was cloned in the BamHI site of plasmid pPATA1 (FIG. 1). Plasmid pPATA 1 is a derivative of plasmid pUC19 and has tuber specific patatin class I promoter SEQ ID No. 7, a polylinker cloning region, and a 35S terminator. From the resulting plasmid the 3.1 kb KpnI fragment containing the patatin promoter, the beps cDNA and the 35S terminator was isolated and inserted in the KpnI site of the plant transformation vector pBKL4 (FIG. 2) to yield plasmid pPPS1 (FIG. 3).

Plasmid pBKL4 is a derivative of plasmid pBIN19 for *Agrobacterium tumefaciens* mediated transformation of plants and harbours a T-DNA region with a β-glucuronidase gene (GUS) transcribed from a 35S promoter and terminated at the nopaline synthase gene terminator, a polylinker cloning region, and a neophosphotransferase gene transcribed from a 35S promoter and terminated at the octopine synthase gene terminator.

EXAMPLE 2

Plasmid pPPL1

Plasmid pPPL1 is a pBKL4 derivative containing the construction: Patatin promoter—Large subunit ADP-glucose pyrophosphorylase cDNA—35S terminator.

The ADP-glucose pyrophophorylase cassette was inserted in the EcoRI site of pBKL4.

The additional elements introduced in the pBKL4 T-DNA by this insertion are described below.

Patatin promoter: The patatin promoter is a tuber specific promoter from potato (Mignery et al. 1988, Gene 62:27–44)—see SEQ ID No. 7.

Large subunit ADP-glucose pyrophosphorylase (bep110): This is a 1.9 kb cDNA fragment encoding the large subunit ADP-glucose pyrophosphorylase from barley endosperm (Villand et al. 1992, Plant Physiol 100: 1617–1618)—see SEQ ID No. 1.

35S terminator: The CAMV 35S terminator (Odell et al. 1985, Nature 313:810–812) is fused to the bepl 10 fragment.

Figure 4:
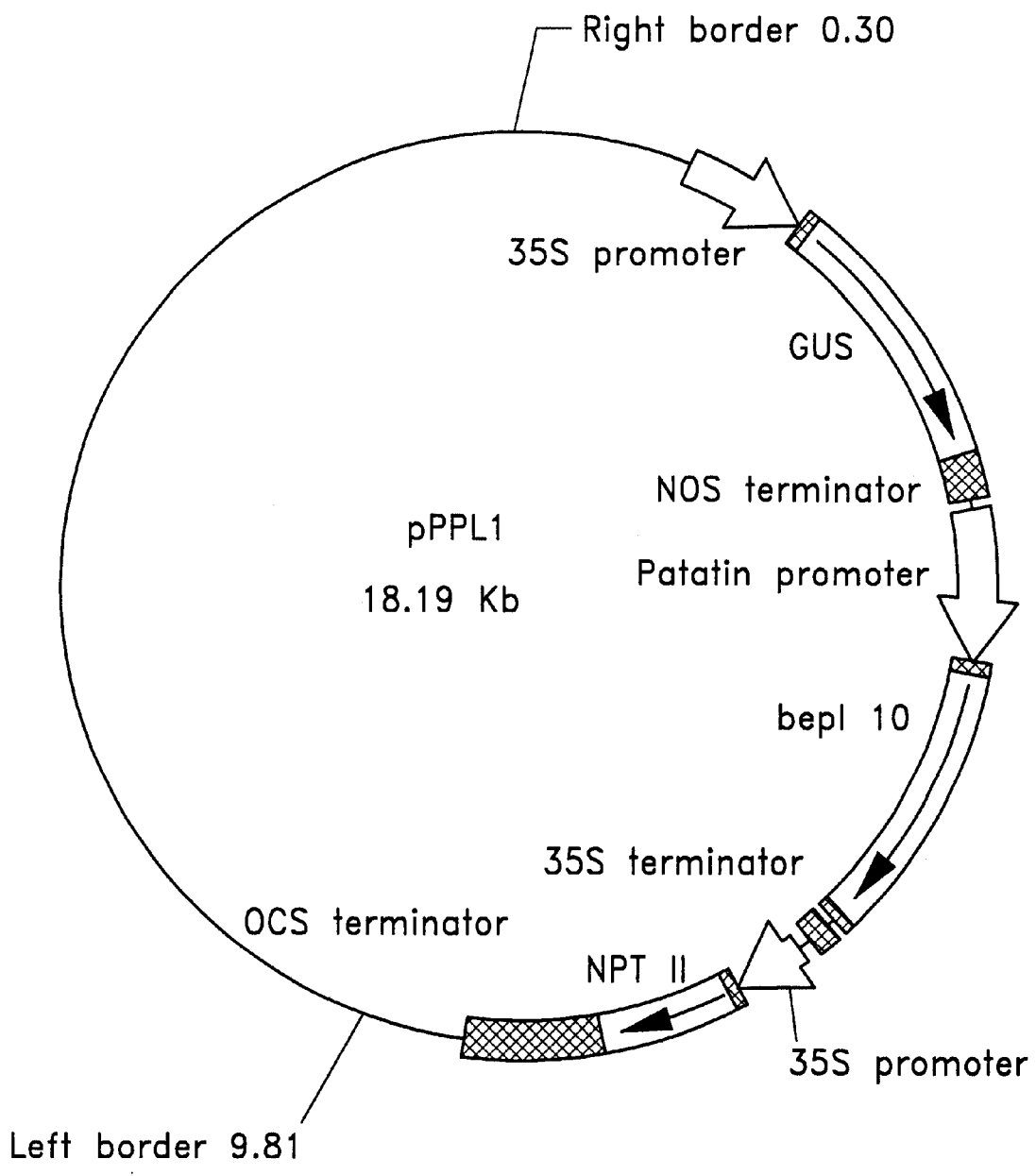
FIG. 4 shows the restriction map for plasmid pPPL1.

In more detail, a 1.9 kb EcoRI-HindIII cDNA fragment encoding the barley endosperm ADP glucose pyrophosphorylase large subunit (bepl) was isolated, the restriction ends were filled in with klenow DNA polymerase, and the blunt ended DNA fragment was cloned in the SmaI site of plasmid pPATA1. From the resulting plasmid the 3.2 kb EcoRI fragment containing the patatin promoter, the bepl cDNA, and the 35S terminator was isolated and inserted in the EcoRI site of the plant transformation vector pBKL4 to yield plasmid pPPL1 (FIG. 4).

EXAMPLE 3

Plasmid pPPL1M

Figure 13:
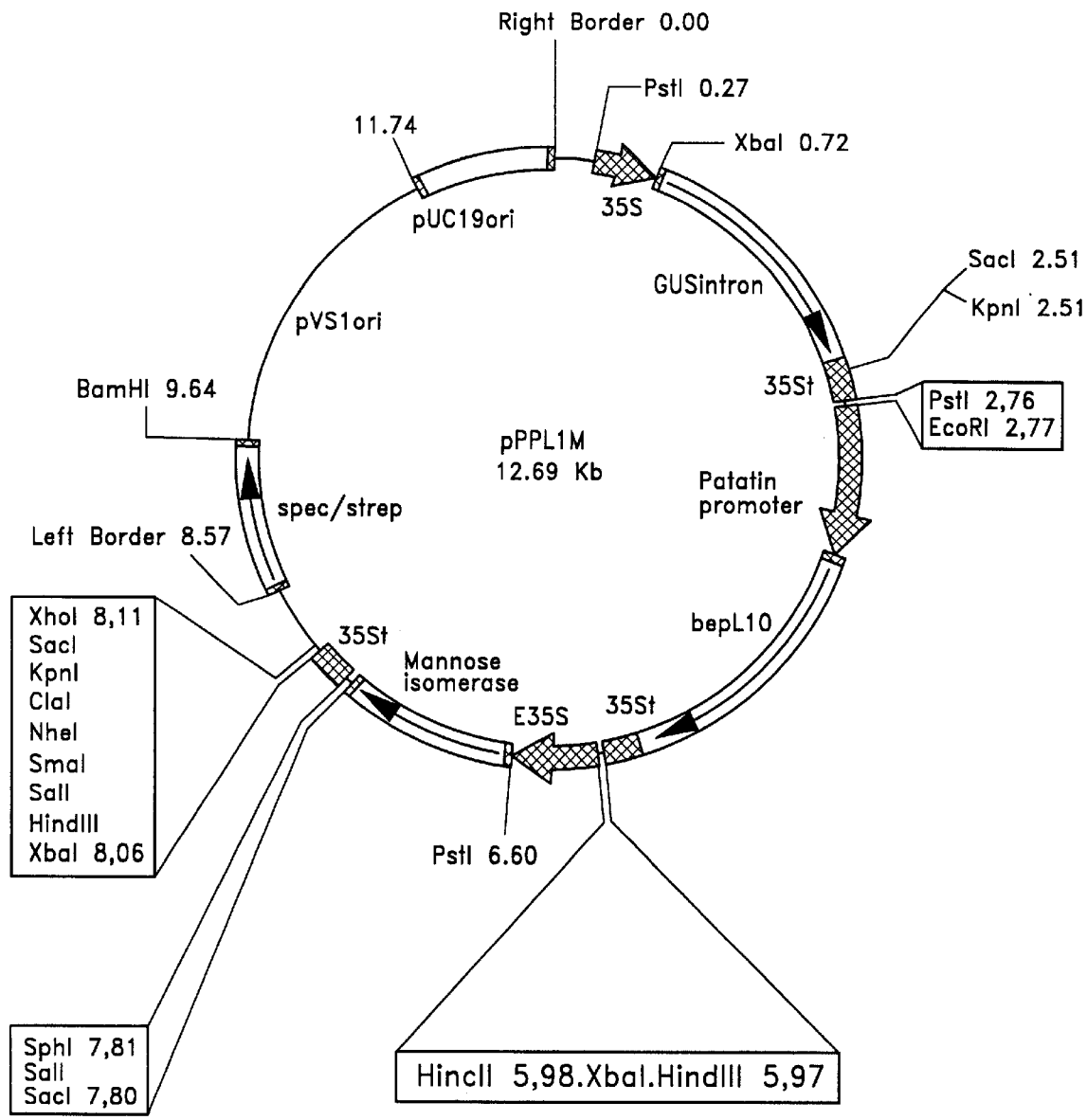
FIG. 13 shows the restriction map for plasmid pPPL1M.

Plasmid pPPL1M (see FIG. 13) is similar to pPPL1 except that the ADP-glucose pyrophosphorylase cassette: Patatin promoter—Large subunit ADP-glucose pyrophosphorylase—35S terminator was inserted in the EcoRI site of pVictorIV SGiN Man.

EXAMPLE 4

Figure 6:
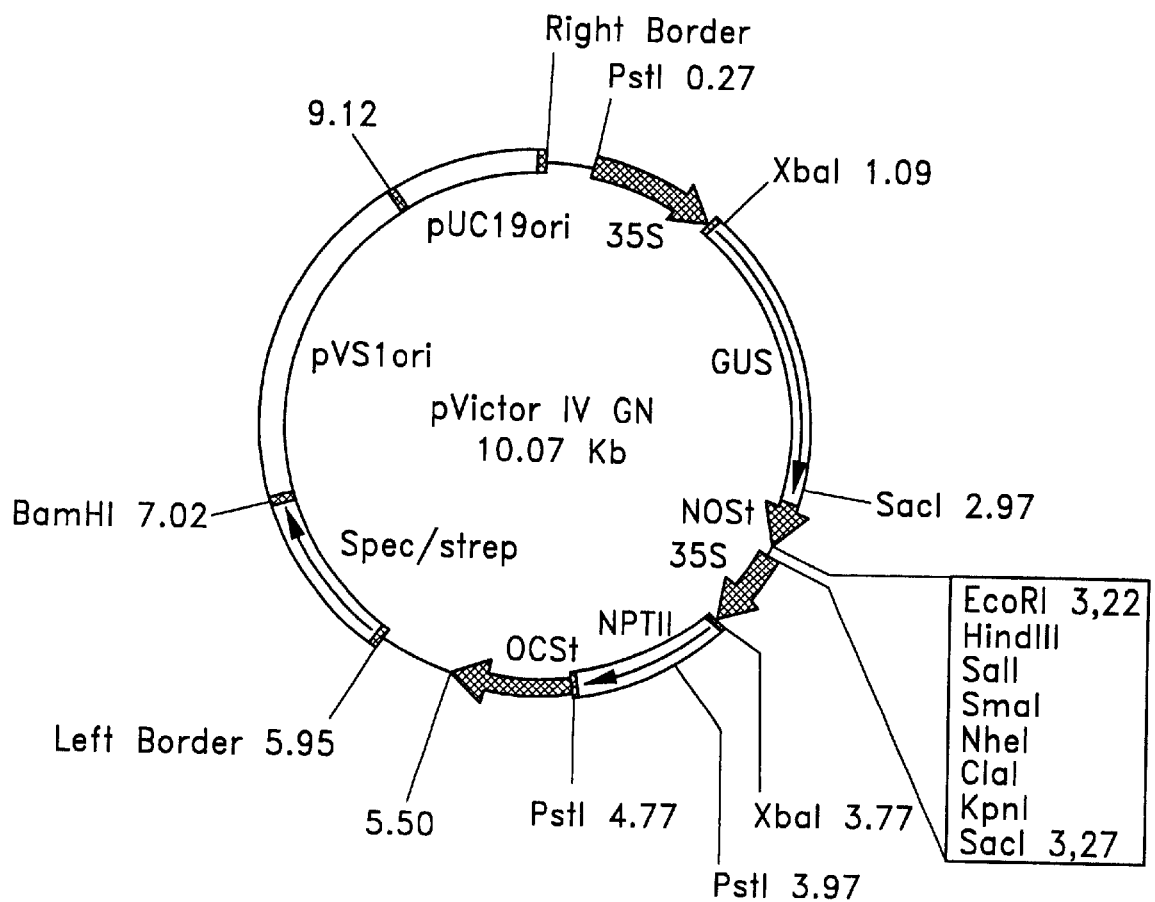
FIG. 6 shows the restriction map for plant transformation vector pVictor IV GN.

Plasmid pVictor IV SGN pVictorIV SGN (FIG. 6) is a vector for Agrobacterium mediated plant transformation, and contains the Ti right and left border sequences from the nopaline type pTiT37 plasmid (Yadav et al. 1982, Proc Natl Acad Sci 79: 6322–6326) flanking the genes encoding kanamycin resistance (NPTII) and B-glucoronidase (GUS).

For replication and maintenance in *E. coli* the plasmid contains the origin of replication from the *E. coli* plasmid pUC19 (pUC19ori) (Yanish-Perron et al. 1985 Gene 33: 103–119), and for replication and maintenance in *Agrobacterium tumefaciens* the plasmid further contains the origin of replication from the Pseudomonas plasmid pVS1 (pVS1ori) (Itoh et al. 1984, Plasmid 11:206–220, Itoh and Haas 1985, Gene 36:27–36). For selection in *E. coli* and *Agrobacterium tumefaciens* the plasmid contains the spectinomycin/streptomycin resistance gene (spec. strep) from the transposon Tn7 encoding the enzyme 3'(9)-O-nucleotidyltransferase (Fling et al. 1985, Nucleic Acids Res 19:7095–7106). The spec/strep resistance gene is fused to the tac promoter for efficient expression in the bacterium.

The T-DNA segment between the right and left border harbours the following genes, which are the only genes transferred to the potato plant via the *Agrobacterium tumefaciens* mediated transformation.

β-glucuronidase (GUS): This segment next to the right border is the β-glucuronidase gene (GUS) from *E. coli* (Jefferson et al., 1986, Proc Natl Acad Sci 83:8447–8451) fused to the CaMV 35S promoter (35S) and 35S terminator (35St) (Odell et al. 1985, Nature 313:810–812).

Multiple cloning sites (MCS): A polylinker containing various restriction endonuclease recognition sites is inserted after the 35S terminator.

Kanamycin resistance (NPTII): The segment next to the MCS is the kanamycin (neomycin) phosphotransferase gene (NPTII) from the transposon Tn5 (Beck et al. 1982 Gene 19:327–336) fused to the CaMV 35S promoter (Odell et al. 1985, Nature 313:810–812) and the terminator of the octopine synthase gene (Caplan et al. 1983, Science 222:815–821).

EXAMPLE 5

Figure 7:
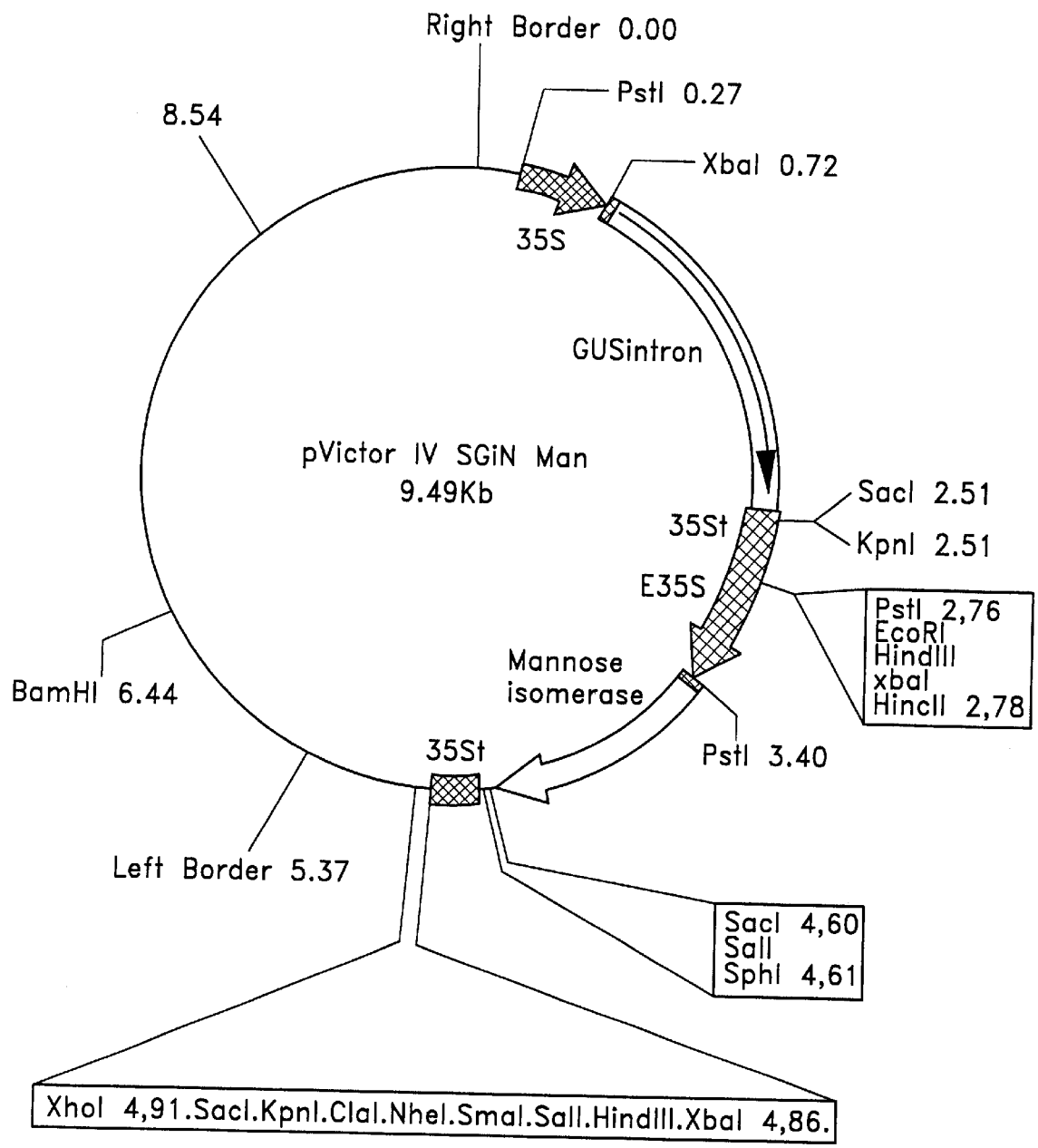
FIG. 7 shows the restriction map for plant transformation vector pVictor IV SGin Man.

Plasmid pVictor IV SGiN Man pVictorIV SGiN Man (FIG. 7) is similar to pVictorIV SGN (Bilag XI) except that the GUS gene is replaced by another GUS gene containing an intron (GUSintron) to prevent expression in bacteria.

Moreover, the kanamycin (neomycin) phosphotransferase gene (NPTII) has been replaced by the mannose-6-phosphate isomerases gene, manA, from *E. coli*.

5β-glucuronidase (GUSintron): This segment next to the right border is the β-glucuronidase gene (GUS) from *E. coli* (Jefferson et al. 1986, Proc Natl Acad Sci 83: 8447–8451) furnished with an intron to prevent expression in bacteria, and fused to the CaMV 35S promoter (35S) and 35S terminator (35St) (Odell et al. 1985, Nature 313:810–812).

Mannose-6-phosphate isomerase: This segment is the mannose-6-phosphate isomerases gene, manA, from *E. coli* (Miles and Guest 1984, Gene 32:41–48) fused to the enhanced 35S promoter (E35S) (Kay et al. 1987, Science 236: 1299–1302) and 35S terminator (35St) (Odell et al. 1985, Nature 313:810–812). The phosphomannose isomerase gene is used as a selection marker to select transgenic shoots on a media containing D-mannose as the carbon source.

B. Attachment of Transit Peptides to the ADP-Glucose Pyrophosphorylase Subunits

EXAMPLE 6

Plasmid pPPS4 pPPS4 (FIG. 9) is a pVictorIV derivative in which a 3 kb KpnI fragment containing the construct:

Patatin promoter—spinach rubisco activase transit peptide—small subunit AGP from barley endosperm—35S terminator is inserted in the KpnI site.

In more detail, the coding region of the barley endosperm ADP glucose pyrophosphorylase small subunit (beps) cDNA was amplified by PCR using the primers:

5' CGG GAT CCA TGG ATG TAC CTT TGG CA 3' (SEQ ID No. 11) and

Figure 5:
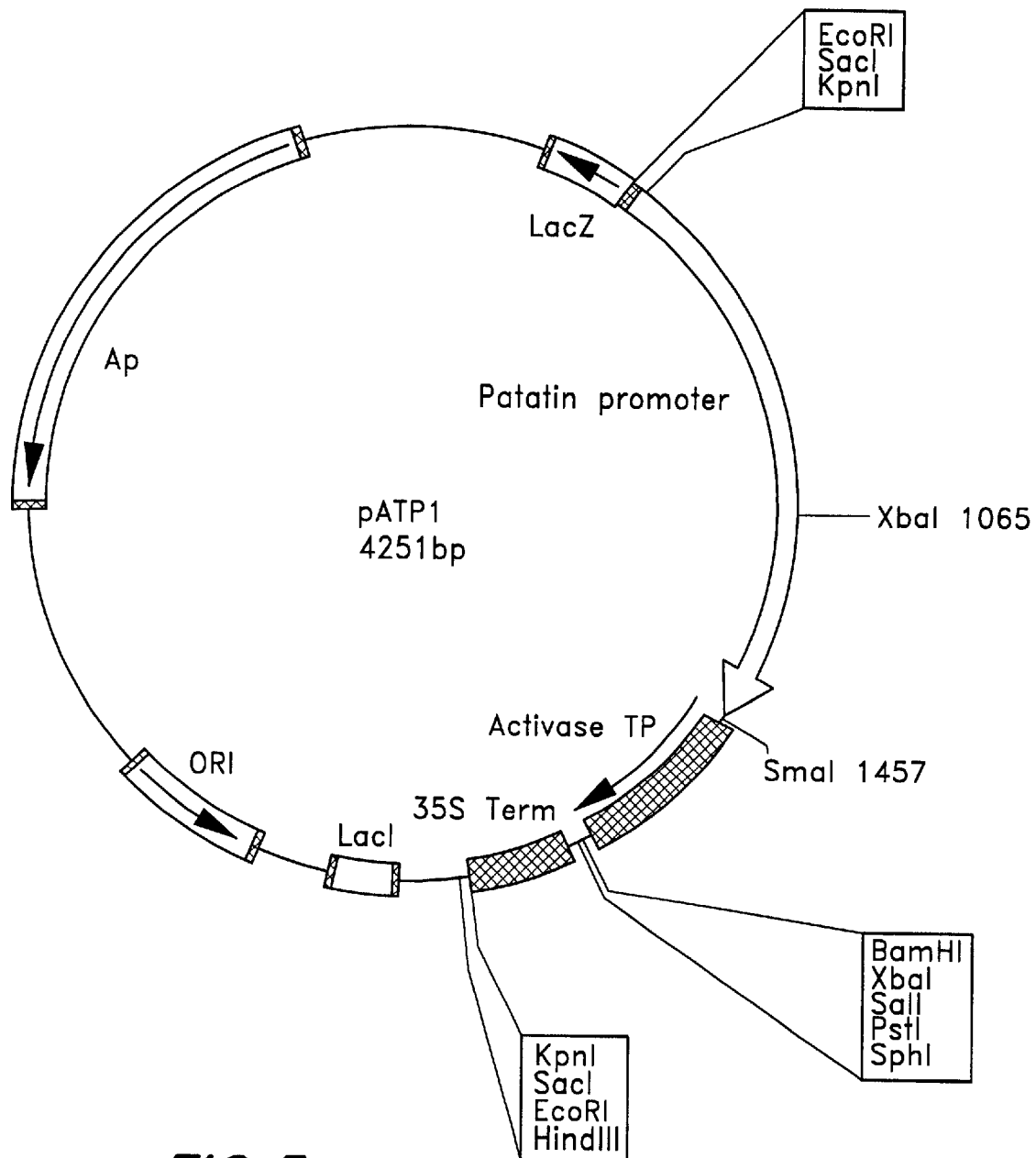
FIG. 5 shows the restriction map for plasmid pATP1.
Figure 9:
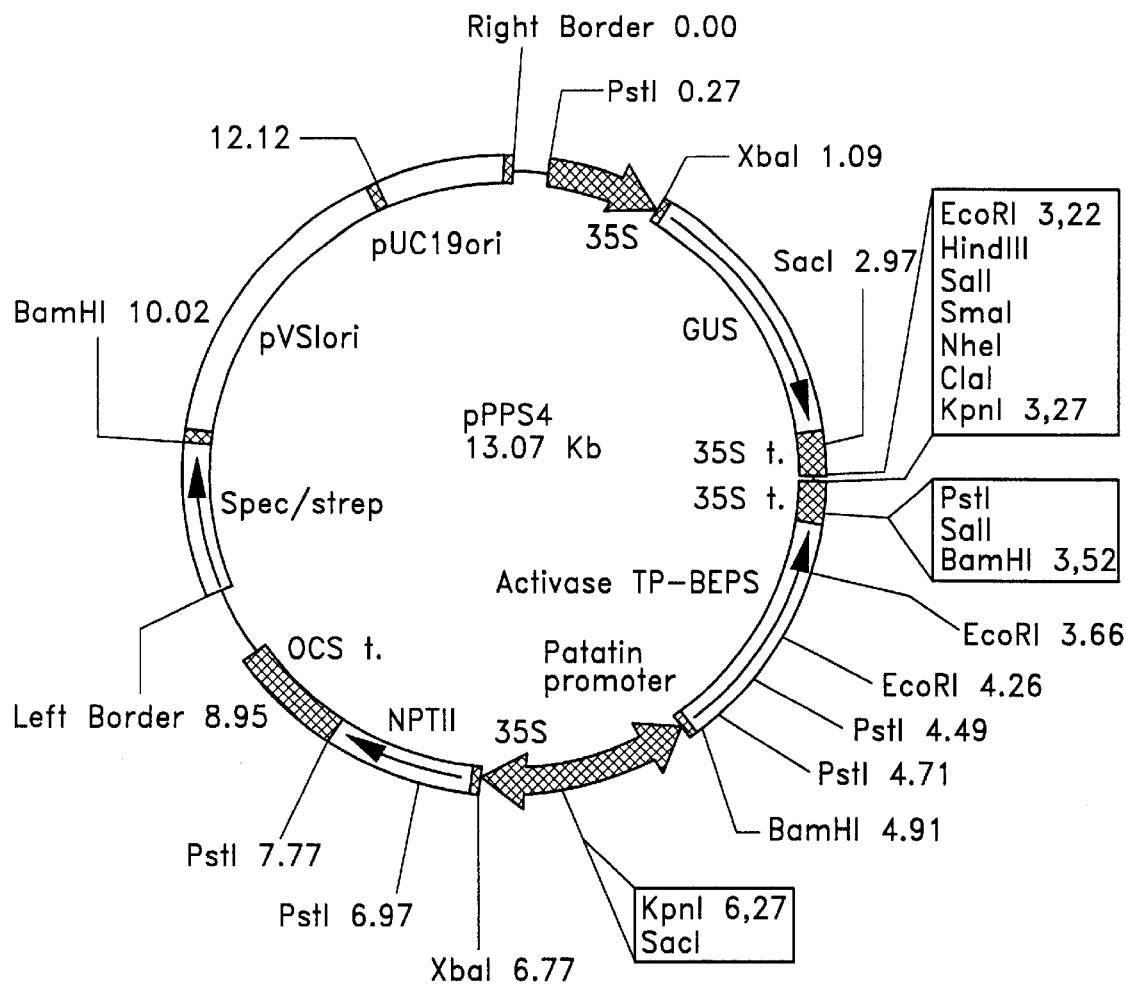
FIG. 9 shows the restriction map for plasmid pPPS4.

5' CGG GAT CCT TAT TTA ATA TGA CTG TTC CAC TAG 3' (SEQ ID No. 12) which provide the PCR fragment with a BamnHI and a NcoI in the 5' end and a BamHI site at the 3' end. The 1.4 kb BamHI fragment containing the entire coding region of the AGP small subunit plus two additional amino acids (G and S) at the amino-terminal end was cloned in the BamHI site of pBluescript II KS to yield plasmid pBBSF. The 1.4 kb BamHI fragment was isolated from pBBSF and cloned in the BamHI site of plasmid pATP1 (FIG. 5). Plasmid pATP1 has a patatin promoter, a 58 amino acid rubisco activase transit peptide DNA and 35 amino acids of the mature enzyme, a BamHI site that facilitates in frame fusion of the small subunit AGP reading frame, and a 35S terminator. The 3 kb KpnI fragment including the patatin promoter, the activase transit peptide, the AGP coding region, and the 35S terminator was isolated from the resulting plasmid and cloned in the KpnI site of the plant transformation vector pVictorIV GN (FIG. 6) to give plasmid pPPS4 (FIG. 9).

Amino Terminal Amino Acid Sequence of the Nibisco Activase—AGP Small Subunit Fusion Enzyme

```
  1 MATAVSTVGA ATRAPLNLNG SSAGASVPTS GELGSSLKKH   40
 41 TNVRFPSSSR TTSMTVKAAE NEEKNTDKWA HLAKDFSDDQ   80
 81 LDIRRGKGMV DSLGSMDVPL ASKVPLPSPS KHEQCNVYSH  120
```

The rubisco activase sequences starts at amino acid residue 1 and ends at leucine residue at 93, while the AGP small subunit sequences begins with the methionine at 96. The rubisco activase transit peptide is cleaved at the alanine residue at 58 leaving the alanine at 59 as the N-terminal amino acid.

The above sequence is listed later on as SEQ ID No. 8.

EXAMPLE 7

Plasmid pPPL4 pPPL4 is a pVictorIV SGiN Man derivative in which a 3.2 kb EcoRI fragment containing the construct:

Patatin promoter—spinach rubisco activase transit peptide—large subunit AGP from barley endosperm—35S terminator is inserted in the EcoRI site.

In more detail, the coding region of the barley endosperm ADP glucose pyrophosphorylase large subunit (bepl) cDNA was amplified by PCR using the primers 5' GCG GAT CCA TAT CGA GTT CAG CGT 3' (SEQ ID No. 13) and 5' CGG GAT CCG CAC AGG TTG TCG CAG AAC 3' (SEQ ID No. 14)

which provide the PCR fragment with a BamHI and a NdeI in the 5' end and a BamHI site at the 3' end. The 1.6 kb BamHI fragment containing the entire coding region of the AGP large subunit plus two additional amino acids (I and H) at the amino-terminal end was cloned in the BamHI site of pBluescript II KS to yield plasmid pBBLF.

Figure 11:
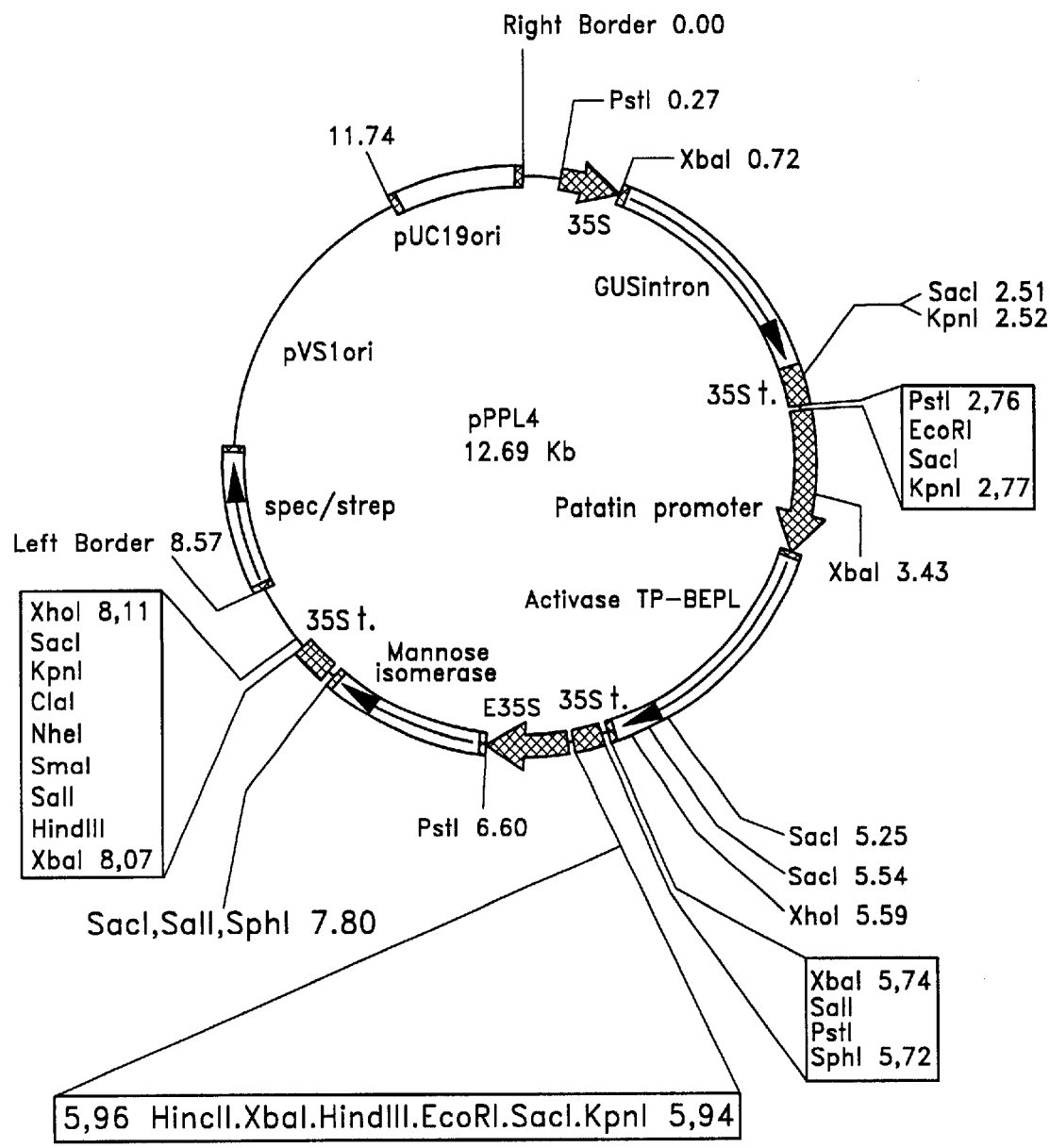
FIG. 11 shows the restriction map for plasmid pPPL4.

The 1.6 kb BamHI fragment was isolated from pBBLF and cloned in the BamHI site of plasmid pATP2. Plasmid pATP2 has a patatin promoter, a 58 amino acid rubisco activase transit peptide DNA and 35 amino acids of the mature enzyme, a BamHI site that facilitates in frame fusion of the large subunit AGP reading frame, and a 35S terminator. The 3 kb EcoRI fragment including the patatin promoter, the activase transit peptide, the AGP coding region, and the 35S terminator was isolated from the resulting plasmid and cloned in the EcoRI site of the plant transformation vector pVictor IV SGiN Man (FIG. 7) to form plasmid pPPL4 (FIG. 11).

Amino Terminal Amino Acid Sequence of the Rubisco Activase—AGP Large Subunit Fusion Eenzyme

```
  1 MATAVSTVGA ATRAPLNLNG SSAGASVPTS GFLGSSLKKH   40
 41 TNVRFPSSSR TTSMTVKAAE NEEKNTDKWA HLAKDFSDDQ   80
 81 LDIRRGKGMV DSLGIHMQFS SVLPLEGKAC VSPVRREGSA  120
```

The rubisco activase sequences starts at amino acid residue 1 and ends at the leucine residue at 93, while the AGP large subunit sequences begins with the methionine at 97. The rubisco activase transit peptide is cleaved at the alanine residue at 58 leaving the alanine at 59 as the N-terminal amino acid. The above sequence is listed later on as SEQ ID No. 9.

EXAMPLE 8

Plasmid pPPL5 pPPL5 is a pVictorIV GIN MAN derivative in which a 3.4 kb EcoRI fragment containing the construct:

Patatin promoter—potato starch branching enzyme amyloplast transit peptide—large subunit AGP from barley endosperm—35S terminator is inserted in the EcoRI site.

The coding region of the barley endosperm ADP glucose pyrophosphorylase large subunit was amplified by PCR using the primers:

5' CGG GAT CCG ATG CAG TTC AGC AGC GTG 3' (SEQ ID No. 15) and

Figure 10:
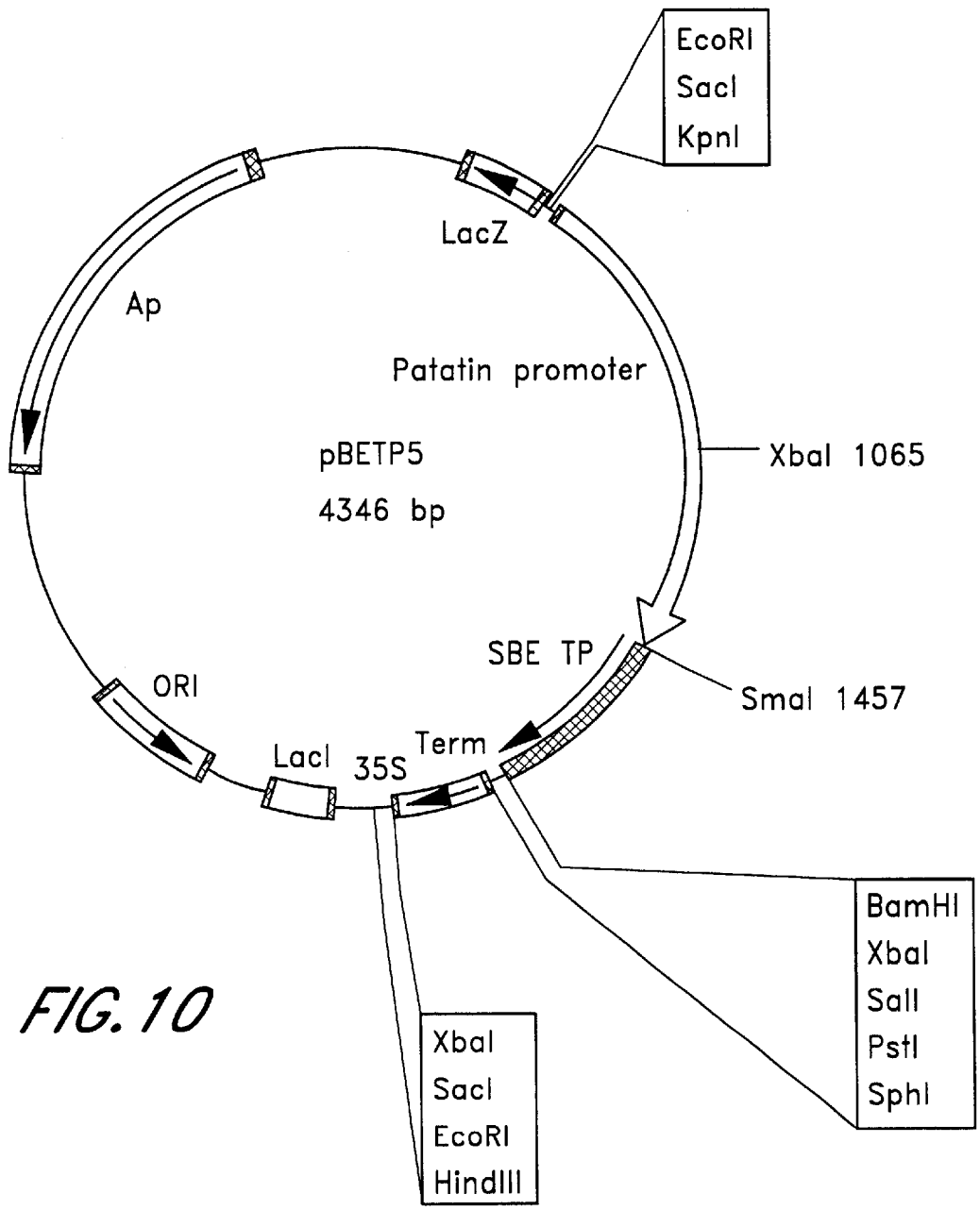
FIG. 10 shows the restriction map for plasmid pBETP5.
Figure 12:
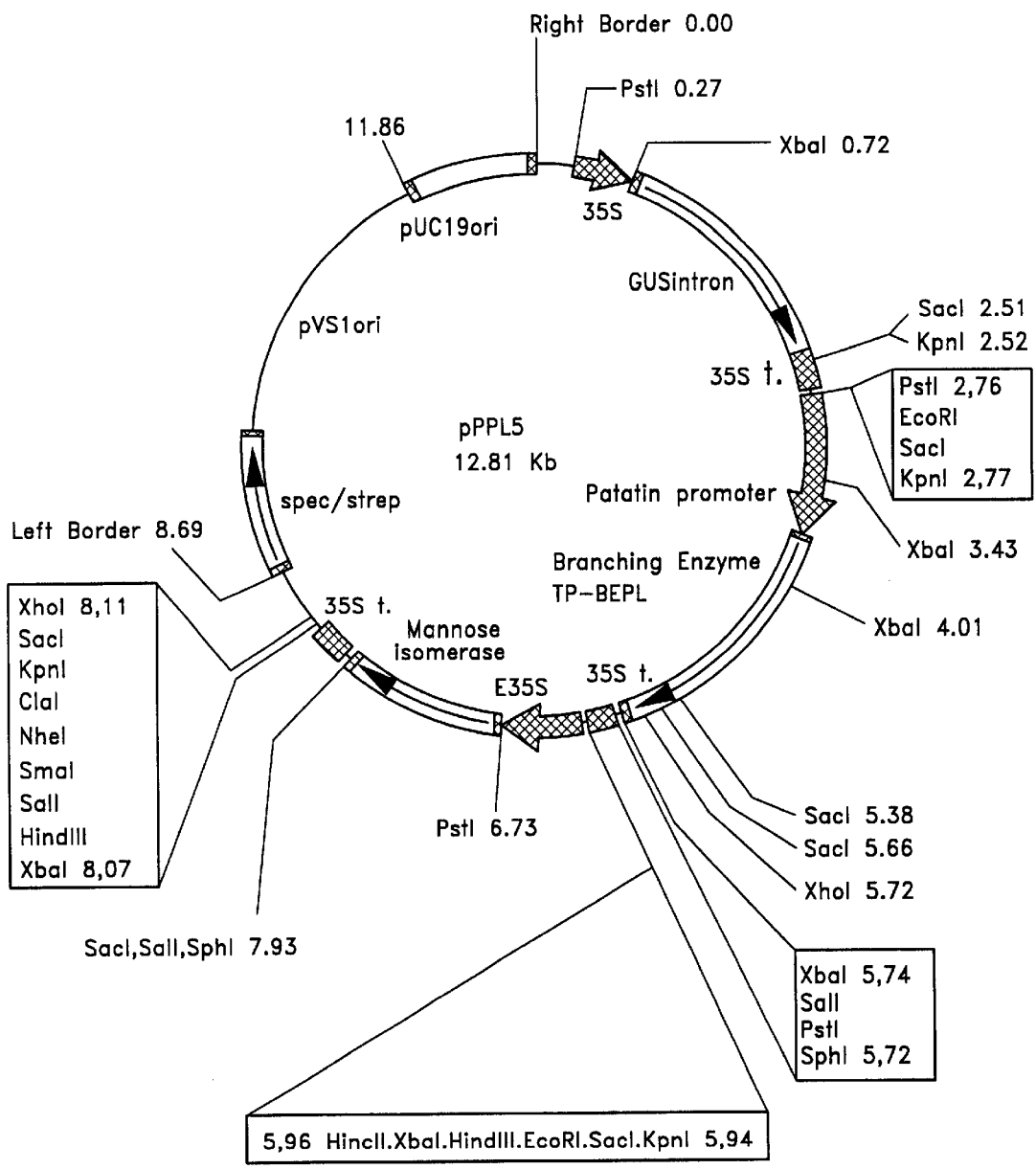
FIG. 12 shows the restriction map for plasmid pPPL5.

5' CGG GAT CCG CAC AGG TTG TCG CAG AAC 3' (SEQ ID No. 14)

which provide a 1.62 kb PCR fragment with BamHI ends. The BamHI fragment containing the entire coding region of the AGP large subunit plus one additional amino acid (P) at the amino terminal end was inserted in the BamHI site of pBETP5 (FIG. 10). In this way the AGP large subunit was fused to the 75 amino acid potato starch branching enzyme transit peptide plus 26 amino acids of the mature branching enzyme. The fusion enzyme is expressed from a patatin promoter and terminated at a 35S terminator. The 3.4 Kb EcoRI fragment from the resulting plasmid (pPBL1) containing the patatin promoter, the starch branching enzyme transit peptide-AGP large subunit fusion enzyme, and the 35S terminator, was inserted in the EcoRI site of the plant transformation vector pVictorIV SGiN Man yielding plasmid pPPL5 (FIG. 12).

Amino Terminal Amino Acid Sequence of the Starch Branching Enzyme—AGP Large Subunit Fusion Enzyme

```
  1 MEINFKVLSK PIRGSFPSFS PKVSSGASRN KICFPSQHST  40
 41 GLKFGSQERS WDISSTPKSR VRKDERMKHS SAISAVLTDD  80
 81 NSTMAPLEED VKTENIGLLN LDPMQFSSVL PLEGKACVSP 120
```

The starch branching enzyme sequences starts at amino acid residue 1 and ends at 103, while the AGP large subunit sequence begins with the methionine at 104. The starch branching enzyme transit peptide is cleaved at the alanine residue (75) leaving the valine residue (76) as the amino terminal amino acid.

The above sequence is listed later on as.SEQ ID No: 10.

C. Production of Transgenic Dotato Plants Containing the AGP-gene

EXAMPLE9

Axenic Stock Cultures

Shoot cultures of Solanum tuberosum 'Bintje' and 'Dianella' are maintained on a substrate (LS) of a formula according to Linsmaier, E. U. and Skoog, F. (1965), Physiol. Plant. 18: 100–127, in addition containing 2 μM silver thiosulphate at 25° C. and 16 h light/8 h dark.

The cultures are subcultured after approximately 40 days. Leaves are cut off the shoots and cut into nodal segments (approximately 0.8 cm) each containing one node.

Inoculation of Potato Tissues

Shoots from approximately 40 days old shoot cultures (height approximately 5–6 cms) were cut into internodal segments (approximately 0.8 cm). The segments are placed into liquid LS-substrate containing the transformed *Agrobacterium tumefaciens* containing the binary vector of interest. The Agrobacterium are grown overnight in YMB-substrate (dipotassiumhydrogen phosphate, trihydrate (0.66 g/l); magnesium sulphate, heptahydrate (0.20 g/l); sodium chloride (0.10 g/l); mannitol (10.0 g/l); and yeast extract (0.40 g/l)) containing appropriate antibiotics (corresponding to the resistance gene of the Agrobacterium strain) to an optical density at 660 nm (OD-660) of approximately 0.8, centrifuged and resuspended in the LS-substrate to an OD-660 of 0.5.

The segments are left in the suspension of Agrobacterium for 30 minutes and then the excess of bacteria are removed by blotting the segments on sterile filter paper.

Co-cultivation

The shoot segments are co-cultured with bacteria for 48 hours directly on LS-substrate containing agar (8.0 g/l), 2,4-dichlorophenoxyacetic acid (2.0 mg/l) and trans-zeatin (0.5 mg/l). The substrate and also the explants are covered with sterile filter papers, and the petri dishes are placed at 25° C. and 16 h light/8 dark.

"Washing" Procedure

After the 48 h on the co-cultivation substrate the segments are transferred to containers containing liquid LS-substrate containing 800 mg/l carbenicillin. The containers are gently shaken and by this procedure the major part of the Agrobacterium are washed off the segments and/or killed.

Selection

After the washing procedure the segments are transferred to plates containing the LSsubstrate, agar (8 g/l), trans-zeatin (1–5 mg/l), gibberellic acid (0.1 mg/l), carbenicillin (800 mg/l), and kanamycin sulphate (50–100 mg/l) or phosphinotricin (1–5 mg/l) or mannose (5 g/l) depending on the vector construction used.

The segments are sub-cultured to fresh substrate each 3–4 weeks.

In 3 to 4 weeks, shoots develop from the segments and the formation of new shoots continues for 3–4 months.

Rooting of Regenerated Shoots

The regenerated shoots are transferred to rooting substrate composed of LS-substrate, agar (8 g/l) and carbenicillin (800 mg/l).

The transgenic genotype of the regenerated shoot are verified by testing the rooting ability on the above mentioned substrates containing kanamycin sulphate (200 mg/l), by performing NPTII assays (Radke, S. E. et al, Theor. Appl. Genet. (1988), 75: 685–694) or by performing a GUS assay on the co-introduced β-glucuronidase gene according to Hodal, L. et al. Pl. Sci. (1992), 87: 115–122 or by assaying the for the expression of the barley AGP mRNA or AGP enzyme activity as described elsewhere. Plants which are not positive in any of these assays are discarded or used as controls.

Transfer to Soil

The newly rooted plants (height approx. 2–3 cms) are transplanted from rooting substrate to soil and placed in a growth chamber (21° C., 16 hour light 200400uE/m2/sec).

When the plants are well established they are transferred to the greenhouse, where they are grown until tubers have developed and the upper part of the plants are senescing.

Harvesting

The potatoes were harvested after about 3 months.

AGP Assay

Tubers from the harvested potato plants were stored at 4° C. AGPase was extracted by homogenization of 10–20 g of thinly sliced potato tubers in 20 ml of buffer containing 25 mM Hepes (pH 7.4) mM mercaptoethanol and 1 mM DTT. Homogenization was performed at 0–4° C. using 30 ml Waring blender at full speed for 15 seconds. Aliquots of crude extract were then immediately centrifuged at maximal speed for 1 min using bench Eppendorf microcentrifuge and then assayed for AGPase activity. Assays were carried out immediately after centrifugation to make sure that the enzyme will not be inactivated during storage.

Assays were carried out in the pyrophosphorolysis direction monitoring glucose-1-P formation at 340 nm (21° C.) using LKB spectrophotometer (Ultrospec II). Assay mixtures (1 ml) contained: 100 mM Mops (pH 7.4), 0.6 mM NAD, 7 mM $MgCl_2$, 1 mM ADP-glucose, 1 mM inorganic pyrophosphate, 10 uM glucose-1,6-biphosphate, 2 units each of glucose-6-P dehydrogenase and phosphoglucomutase. In some instances, 2 mM 3-phosphoglyceric acid (PGA) was added to assays. Assays were run (–PGA) for ca. 5 min, and then PGA was added and assays were monitored for another 5–10 min. Rates were usually linear during the time-course of assays. One unit of AGPase activity corresponds to the amount of enzyme producing 1 umole of NADH under assay conditions.

Starch Analysis

The starch contents of potato tubers was determined according to a method which was designed and proposed by the Dutch-German working group "Standardization" and published in "Methods of assessment for potatoes and potato products". The method was developed for use with a sample size of 5000 g but we scaled the method down for use with potato tubers from a single plant, usually between 20 and 200 g.

All potatoes from a plant are washed and dried with a cloth before weighing (a grams) on an electronic balance. Later, the tubers are weighed again, but this time on a balance with two metal baskets of which one is immersed in a water basin. The potato tubers are placed in the bucket in water, and their weight (b grams) in water is determined.

The under-water weight of a sample is calculated at 5000 b/a grams. From tables showing the relation between under-water weight, dry matter and starch content, the two latter figures can be determined.

This procedure is described in more detail by W. A. Gould in Chipping Potato Handbook, ed. Gould, W. A. The Snack Food Association, Vermont, 1989, pp 18–22, in an article entitled "Specific gravity, its measurement and use".

Results

AGPase levels and starch levels were increased with the constructs of the present invention, particularly in the absence of PGA, especially with the constructs coding for the large sub-unit and in particular the constructs coding for a transit peptide.

In this regard, some results are shown in Table I (below) for transformed potatoes comprising constructs derived from plasmids pPPS4 and pPPL4.

TABLE I

STARCH CONTENT IN TRANSFORMED POTATOES (TRANS) COMPARED TO CONTROL NATIVE POTATOES GROWN UNDER THE SAME CONDITIONS

| Sample | % Overall Starch Content | % Starch Content vis-a-vis Control |
|---|---|---|
| Control | 16 | 100 |
| Trans 1 | 19 | 119 |
| Trans 2 | 23 | 144 |
| Trans 3 | 26 | 163 |
| Trans 4 | 19 | 119 |
| Trans 5 | 26 | 163 |
| Trans 6 | 24 | 150 |
| Trans 7 | 21 | 131 |
| Trans 8 | 17 | 106 |
| Trans 9 | 21 | 131 |

The above results clearly show that the average starch level in the transgenic potatoes comprising constructs derived from plasmids pPPS4 and pPPL4 are increased to about 136% of that found in native potatoes.

Furthermore, the average starch level for the upper two quartiles for the transgenic potatoes comprising constructs derived from plasmids pPPS4 and pPPL4 is about 155% of that found in native potatoes.

Each of these findings is significant.

Other modifications of the present invention will be apparent to those skilled in the art without departing from the scope of the invention.

What is claimed:

1. A method of targeting an exogenous protein to the amyloplast of plants or plant cells which comprises introducing into the plant or plant cell a recombinant DNA construct containing a DNA sequence encoding a potato starch branching enzyme transit peptide, said DNA sequence encoding a potato starch branching enzyme transit peptide comprising the sequence identified as SEQ ID NO: 5 or an allelic variant thereof wherein said allelic variant has a non-critical allelic variation such that said allelic variant has at least 80% homology to the entire sequence identified as SEQ ID NO.: 5, said DNA encoding said potato starch branching enzyme transit peptide being operably linked to an exogenous DNA sequence encoding the exogenous protein and operably linked to a promoter, wherein said potato starch branching enzyme transit peptide targets said exogenous protein to the amyloplast of plants or plant cells.

2. A method according to claim 1, wherein said potato starch branching enzyme transit peptide comprises the amino acid sequence identified as SEQ ID NO: 6.

3. A method of targeting an exogenous protein to the amloplast of plants or plant cells which comprises introducing into the plant or plant cell a recombinant DNA construct containing a DNA sequence encoding a potato starch branching enzyme transit peptide, said DNA sequence encoding a potato starch branching enzyme transit peptide comprising nucleotides 121–346 of the sequence identified as SEQ ID NO.: 5, said DNA encoding said potato starch branching enzyme transit peptide being operably linked to an exogenous DNA sequence encoding the exogenous protein and operably linked to a promoter, wherein said potato starch branching enzyme transit peptide targets said exogenous protein to the amyloplast of plants or plant cells.

4. A method of targeting an exogenous protein to the amyloplast of plants or plant cells which comprises introducing into the plant or plant cell a recombinant DNA construct containing a DNA sequence encoding a potato starch branching enzyme transit peptide comprising amino acids 1–75 of SEQ ID NO: 6, said DNA encoding said potato starch branching enzyme transit peptide being operably linked to an exogenous DNA sequence encoding the exogenous protein and operably linked to a promoter, wherein said potato starch branching enzyme transit peptide targets said exogenous protein to the amyloplast of plants or plant cells.

5. A method of targeting an exogenous protein to the amyloplast of plants or plant cells which comprises introducing into the plant or plant cell a recombinant DNA construct containing a DNA sequence encoding a potato starch branching enzyme transit peptide comprising an allelic variant of the amino acid sequence identified as SEQ ID NO.: 6, wherein said allelic variant has a non-critical allelic variation such that said allelic variant has at least 80% homology to the entire sequence identified as SEQ ID NO.: 6, said DNA encoding said potato starch branching enzyme transit peptide being operably linked to an exogenous DNA sequence encoding the exogenous protein and operably linked to a promoter, wherein said potato starch branching enzyme transit peptide targets said exogenous protein to the amyloplast of plants or plant cells.

6. A method of targeting an exogenous protein to the amyloplast of plants or plant cells which comprises introducing into the plant or plant cell a recombinant DNA construct containing a DNA sequence encoding a potato starch branching enzyme transit peptide, said DNA sequence encoding a potato starch branching enzyme transit peptide comprising an allelic variant of nucleotides 121–346 of SEQ ID NO.: 5 wherein said allelic variant has a non-critical allelic variation such that said allelic variant has at least 80% homology to the entire sequence of nucleotides 121–346 of SEQ ID NO.: 5, said DNA encoding said potato starch branching enzyme transit peptide being operably linked to an exogenous DNA sequence encoding the exogenous protein and operably linked to a promoter, wherein said potato starch branching enzyme transit peptide targets said exogenous protein to the amyloplast of plants or plant cells.

7. A method of targeting an exogenous protein to the amyloplast of plants or plant cells which comprises introducing into the plant or plant cell a recombinant DNA construct containing a DNA sequence encoding a potato starch branching enzyme transit peptide comprising an allelic variant of amino acids 1–75 of SEQ ID NO.: 6 wherein said allelic variant has a non-critical allelic variation such that said allelic variant has at least 80% homology to the entire sequence of amino acids 1–75 of SEQ ID NO.: 6, said DNA encoding said potato starch branching enzyme transit peptide being operably linked to an exogenous DNA sequence encoding the exogenous protein and operably linked to a promoter, wherein said potato starch branching enzyme transit peptide targets said exogenous protein to the amyloplast of plants or plant cells.

* * * * *